United States Patent [19]

Miyazawa et al.

[11] Patent Number: 5,574,182
[45] Date of Patent: Nov. 12, 1996

[54] OPTICALLY ACTIVE COMPOUNDS HAVING PLURAL CHIRAL CENTERS AND PRODUCTION THEREOF

[75] Inventors: Kazutoshi Miyazawa; Naoyuki Yoshida, both of Ichihara, Japan

[73] Assignee: Chisso Corporation, Osaka-fu, Japan

[21] Appl. No.: 380,519

[22] Filed: Jan. 30, 1995

Related U.S. Application Data

[62] Division of Ser. No. 257,666, Jun. 8, 1994, Pat. No. 5,411,877, which is a division of Ser. No. 35,889, Mar. 23, 1993, Pat. No. 5,348,870, which is a division of Ser. No. 612,146, Nov. 13, 1990, abandoned.

[30] Foreign Application Priority Data

Nov. 14, 1989 [JP] Japan .................... 1-295816

[51] Int. Cl.$^6$ .................................. C07C 69/66
[52] U.S. Cl. ................ 560/179; 560/183; 560/184
[58] Field of Search ........................ 560/179, 183, 560/184; 435/135

[56] References Cited

U.S. PATENT DOCUMENTS

| | | | |
|---|---|---|---|
| 2,854,460 | 9/1958 | Hennes et al. | 260/340.2 |
| 3,503,993 | 3/1970 | Blume | 260/340.2 |
| 4,864,037 | 9/1989 | Schaffner et al. | 549/274 |
| 4,916,074 | 4/1990 | Yoshida et al. | 435/280 |
| 4,996,158 | 2/1991 | Oda et al. | 435/280 |
| 5,084,392 | 1/1992 | Miyazawa et al. | 435/280 |
| 5,128,252 | 6/1992 | Miyazawa et al. | 435/134 |
| 5,138,074 | 8/1992 | Bellis et al. | 549/274 |
| 5,319,107 | 6/1994 | Benecke et al. | 549/274 |
| 5,326,887 | 7/1994 | Di Cosimo et al. | 549/274 |
| 5,371,014 | 12/1994 | Matsuyama et al. | 435/280 |

FOREIGN PATENT DOCUMENTS

0244143  11/1987  European Pat. Off. .

OTHER PUBLICATIONS

Bulletin of the Chemical Society of Japan, vol. 62, No. 4, Apr. 1989, pp. 1179–1187.
Chemistry Letters, vol. 1982, 1982, pp. 1799–1802.
Tetrahedron Letters, vol. 27, No. 27, 1986, pp. 3155–3156.
Agricultural and Biological Chemistry, vol. 54, No. 7, Jul. 1990, pp. 1753–1762.
Helvetica Chimica Acta, vol. 69, 1986, pp. 1147–1152.
Patent Abstracts of Japan, vol. 12, No. 283 (C–518)[3130], Aug. 3, 1988.

*Primary Examiner*—Brian M. Burn
*Attorney, Agent, or Firm*—Wenderoth, Lind & Ponack

[57] ABSTRACT

An ester is caused to act on a 2-substituted-3-hydroxycarboxylic acid ester as a racemate in the presence of hydrolase under substantially anhydrous conditions to effect a transesterification resulting in the resolution.

The compound thus resolved is converted to an optically active 2,6-cis-2,5,6-substituted-1,3-dioxan-4-one and the resulting compound is recrystallized to give optically active 5,6-anti-2,5,6-substituted-1,3-dioxan-4-one and 5,6-syn-2,5,6-substituted-1,3-dioxan-4-one. Thus an optically active compound having plural chiral centers.

Further, an optically active 2,5,6-substituted-1,3-dioxan-4-one obtained by transesterification and recrystallization is reacted with an alcohol to produce an optically active 2-substituted-3-hydroxycarboxylic acid ester.

2 Claims, 9 Drawing Sheets

OPTICALLY ACTIVE COMPOUNDS HAVING PLURAL CHIRAL CENTERS AND PRODUCTION THEREOF

This is a divisional application of now allowed Ser. No. 08/257,666 filed Jun. 8, 1994, now U.S. Pat. No. 5,411,977 which is a divisional application of Ser. No. 08/035,889 filed Mar. 23, 1993, now U.S. Pat. No. 5,348,870, which is a divisional application of now abandoned Ser. No. 07/612,146 filed Nov. 13, 1990.

BACKGROUND OF THE INVENTION

1. Field of the Invention

The present invention relates to an optically active compound having plural chiral centers and processes for producing said compound. More particularly it relates to an optically active 2-substituted-3-substituted-carboxylic acid ester and an optically active 2,6-cis-2,5,6-substituted-1,3-dioxan-4-one and processes for producing the compound.

2. Description of Related Art

Optically active compounds, in particular, optically active 2-substituted-3-hydroxycarboxylic acid esters and their esters, are considered useful as medicines, starting materials or intermediates for producing biologically active compounds such as medicines, agricultural chemicals, and the like and functional materials.

However, such optically active compounds have two chiral centers resulting in the presence of four stereo-isomers and therefore, it is necessary for exhibiting sufficient biological activities or sufficient functions that only one stereoisomer is present in a large amount. Consequently, efficiently separating the four stereo-isomers from one another is a big problem.

In order to produce optically active compounds, for example, an asymmetric synthesis is carried out; racemic compounds produced by ordinary chemical synthesis are subjected to optical resolution; or an optically active compound is converted to another desired optically active compound by a stereochemical method.

In particular, optically active methyl 2-methyl-3-hydroxybutanoate can be produced by firstly forming the salt and then resolving it according to recrystallization [A. Tai and M. Imaida, Bull. Chem. Soc. Jpn., 51, 1114 (1978)], or ethyl (2R, 3R)-2-propyl-3-hydroxypentanoate can be produced by alkylation with lithium diisopropylamide (hereinafter called "LDA") [G. Frater, Helv. Chim. Acta., 62, 2829 (1979)].

It is difficult to carry out in an industrial scale the above-mentioned method where the salt is first prepared followed by recrystallization, and moreover only a limited number of compounds can be resolved by recrystallization. The alkylation with LDA requires a reaction condition of extremely low temperatures (−78° C. to −50° C.) and, in addition, an optically active 3-hydroxycarboxylic acid ester as a starting materials. Further, in the above-mentioned reaction, only the anti-form can be obtained and the selectivity is not 100%, but anti-form: syn-form=94:6.

Some 1,3-dioxan-4-one compounds have already been prepared and the cis/trans selectivity is utilized for studying the synthesis of optically active secondary alcohols and the like [S. L. Schreiber et al., Tetrahedron Lett., 27, 2945 (1986); D. Seebach et al, Angew. Chem. Int. Ed. Engl., 25, 178 (1986)].

However, there is little searching for optically active compounds having a substituent at the 5-position. The only one is that where the unsubstituted carbon atom at the 5-position is alkylated by using LDA [D. Seebach, Helv. Chim. Acta., 69, 1147 (1986)], but LDA has drawbacks that, as mentioned above, it should be used in a reaction at extremely low temperatures such as, for example, −75° C. and only one enantiomer can be obtained.

SUMMARY OF THE INVENTION

An object of the present invention is to provide a novel optically active compound having plural chiral centers, more particularly, a novel optically active 1,3-dioxan-4-one compound which may be an intermediate for producing optically active 2-substituted-3-substituted-carboxylic acid esters and optically active 2-substituted-3-hydroxycarboxylic acids.

Another object of the present invention is to provide a process for producing optically active 2-substituted-3-hydroxycarboxylic acid esters and a process for producing an intermediate for producing said esters.

A further object of the present invention is to provide a process for resolving a racemate of a 2-substituted-3-hydroxycarboxylic acid ester.

According to one aspect of the present invention, there is provided a first optically active 2-substituted-3-substituted-carboxylic acid ester having plural chiral centers of the general formula,

which may include more particularly compounds of the following formulas (2)–(7),

where $R^1$ and $R^2$ are independently selected from the group consisting of alkyl, alkenyl, and alkynyl, having 1–40 carbon atoms where, the carbon chain may contain at least one member selected from the group consisting of halogen, cyano, oxygen, nitrogen, silicon sulfur, benzene ring, cyclohexane ring, pyridine ring, pyrimidine ring, pyridazine ring, pyrazine ring, dioxane ring, bicyclooctane ring, and the rings with at least one substituent; $R^3$ is selected from the group consisting of alkyl, alkenyl and alkynyl, having 3–40 carbon atoms ; X is hydrogen or alkanoyl having 2–40 carbon atoms; and the carbon atom with a sign, *, is an asymmetic carbon; preferably, $R^1$ and $R^2$ are independently selected from the group consisting of alkyl, alkenyl and alkynyl, having 1–40 carbon atoms ; $R^3$ is selected from the group consisting of alkyl, alkenyl and alkynyl, having 3–40 carbon atoms ; and X is hydrogen or alkanoyl having 2–40 carbon atoms ; more preferably, $R^1$ and $R^2$ are independently selected from the group consisting of alkyl and alkenyl having 1–40 carbon atoms ; $R^3$ is alkyl having 3–40 carbon atoms ; and X is hydrogen or alkanoyl having 2–40 carbon atoms ; preferably, $R^1$ and $R^2$ have 1–20 carbon atoms, more preferably, 1–10 carbon atoms ; preferably, $R^3$ has 3–20 carbon atoms and more preferably, 3–10 carbon atoms.

According to another aspect of the present invention, there is provided a second optically active compound having plural chiral centers of the general formula,

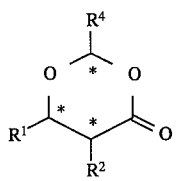
(11)

which may include more particularly compounds of the following formulas,

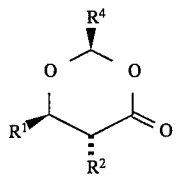
(12)

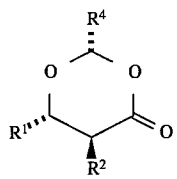
(13)

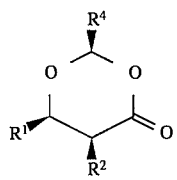
(14)

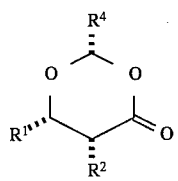
(15)

where $R^1$, $R^2$ and $R^4$ are independently selected from the group consisting of alkyl, alkenyl, and alkynyl, having 1–40 carbon atoms where, the carbon chain may contain at least one member selected from the group consisting of halogen, cyano, oxygen, nitrogen, silicon, sulfur, benzene ring, cyclohexane ring, pyridine ring, pyrimidine ring, pyridazine ring, pyrazine ring, dioxane ring, bicyclooctane ring, and the rings with at least one substituent; and the carbon atom with a sign, *, is an asymmetric carbon; $R^4$ is preferably trihalomethyl, and $R^1$ and $R^2$ are preferably selected from the group consisting of $C_1$–$C_{20}$ alkyl and $C_1$–$C_{20}$ alkenyl According to a further object of the present invention, there is provided a first process for producing an optically active compound having plural chiral centers which comprises causing an ester to act on a 2-substituted-3-hydroxycarboxylic acid ester as racemate of the general formula (8)

(8)

in the presence of a hydrolase under substantially anhydrous conditions to effect transesterification and resolving into a compound of formula (6-1) and a compound of formula (7-2), or a compound of formula (6-2) and a compound of formula (7-1),

(6-1)

(6-2)

(7-1)

(7-2)

converting said compounds to an optically active 2,6-cis-2,5,6-substituted-1,3-dioxan-4-one of the general formula (9),

(9)

and separating the resulting compound into crystal and a mother liquor for recrystallization by recrystallization to give the respective 2,5,6-substituted-1,3-dioxan-4one compounds having the absolute configurations shown by the following formulas,

(12)

and

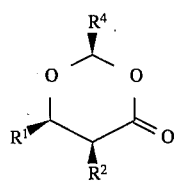 (14)

or

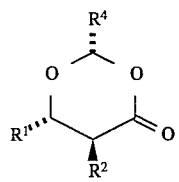 (13)

and

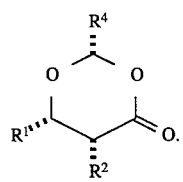 (15)

More particularly, the optically active 2,6-cis-2,5,6-substituted-1,3-dioxan-4-one of the formula (9) can be produced by hydrolysis or hydrolysis plus alcoholysis of compounds (6-1), (6-2), (7-1) or (7-2) produced by resolution, to form optically active 2-substituted-3-hydroxycarboxylic acids of the formulas (19-a) and (19-b),

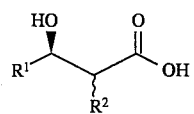 (19-a)

and

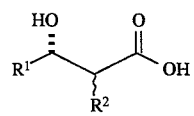 (19-b)

and reacting an aldehyde of the formula, $$R^4CHO \quad (22)$$

with said acids to give the optically active 2,6-cis-2,5,6-substituted-1,3-dioxan-4-one, in the above formulas, formula (9) is a mixture of compounds of formulas (12) and (14) or a mixture of compounds of formulas (13) and (15), $R^1$, $R^2$ and $R^4$ are independently selected from the group consisting of alkyl, alkenyl, and alkynyl, having 1–40 carbon atoms where, the carbon chain may contain at least one member selected from the group consisting of halogen, cyano, oxygen, nitrogen, silicon, sulfur, benzene ring, cyclohexane ring, pyridine ring, pyrimidine ring, pyridazine ring, pyrazine ring, dioxane ring, bicyclo-octane ring, and the rings with at least one substituent; $R^5$ is selected from the group consisting of alkyl, alkenyl and alkynyl, having 1–40 carbon atoms, X' is alkanoyl having 2–40 carbon atoms, and the carbon atom with a sign, *, is an asymmetric carbon.

According to a still further aspect of the present invention, there is provided a second process for producing an optically active compound having plural chiral centers which comprises reacting a 2,5,6-substituted-1,3-dioxan-4-one having absolute configuration as shown in formulas (12), (13), (14) and (15) above with an alcohol of the formula, $$R^5OH \quad (23)$$

to produce a 2-substituted-3-hydroxycarboxylic acid ester having absolute configuration of the general formula,

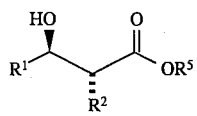 (2')

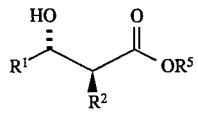 (3')

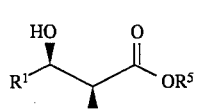 (4')

or

 (5')

where $R^1$ $R^2$ and $R^5$ are as defined above

According to still another aspect of the present invention, there is provided a first process for resolving a 2-substituted-3-hydroxycarboxylic acid ester as racemate which comprises causing an ester to act on the 2-substituted-3-hydroxycarboxylic acid ester as racemate of the general formula,

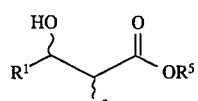 (8)

in the presence of a hydrolase under substantially anhydrous conditions to effect transesterification to resolve the racemate into the compounds of the following formulas (6-1) and (7-2), or the compounds of the following formulas (6-2) and (7-1)

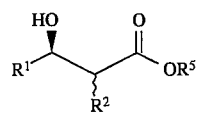 (6-1)

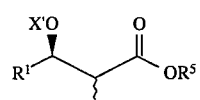 (6-2)

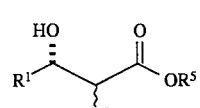 (7-1)

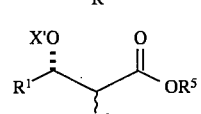 (7-2)

where $R^1$ and $R^2$ are independently selected from the group consisting of alkyl, alkenyl, and alkynyl, having 1–40 carbon atoms where, the carbon chain may contain at least one member selected from the group consisting of halogen, cyano, oxygen, nitrogen, silicon, sulfur, benzene ring, cyclohexane ring, pyridine ring, pyrimidine ring, pyridazine ring, pyrazine ring, dioxane ring, bicyclooctane ring, and the rings with at least one substituent; $R^5$ is selected from the group consisting of alkyl, alkenyl and alkynyl, having 1–40 carbon atoms; and X' is alkanoyl having 2–40 carbon atoms.

According to a still further aspect of the present invention, there is provided a second process for resolving a 2-substituted-3-hydroxycarboxylic acid ester which comprises hydrolyzing a 2-substituted-3-hydroxycarboxylic acid ester as racemate of the general formula,

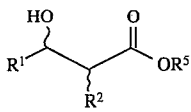  (8)

to form a 2-substituted-3-hydroxycarboxylic acid of the general formula,

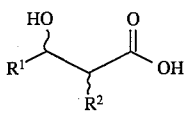  (19)

causing an aldehyde of the general formula,

  (22)

to act on said carboxylic acid to form a 2,5,6-substituted-1,3-dioxan-4-one of the formula,

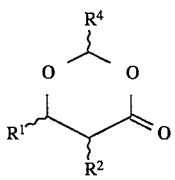  (10)

separating the resulting product into crystals and a mother liquor for recrystallization by recrystallization, and reacting the resulting crystal 5 and mother liquor residue with an alcohol of the formula

  (23)

to effect a ring-opening reaction resulting in resolving the racemate of the formula (8) into 2,3-syn-2-substituted-3-hydroxycarboxylic acid esters of the formulas,

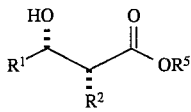  (5')

and

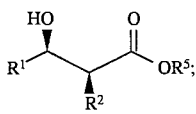  (4');

or 2,3-anti-2-substituted-3-hydroxycarboxylic acid esters of the formulas,

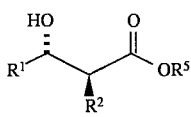  (3')

and

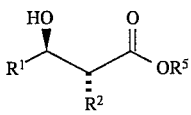  (2')

where $R^1$ $R^2$ and $R^5$ are as defined above.

DESCRIPTION OF THE PREFERRED EMBODIMENTS

Figure 1:
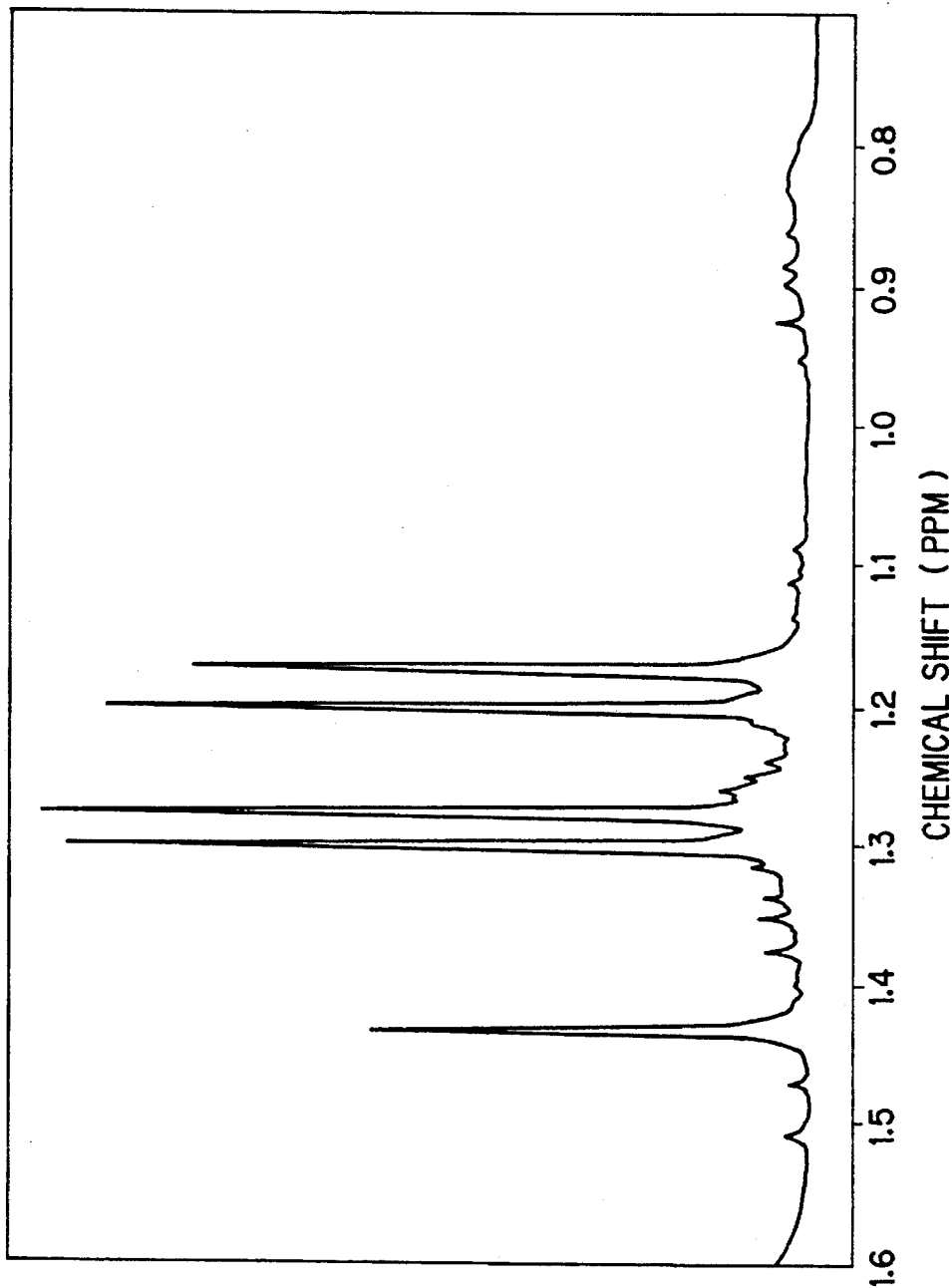
FIG. 1 shows a $^1$H-NMR spectrum of R-(+)-methoxytrifluoromethylphenyl acetic acid (hereinafter referred to as "(+)-MTPA") ester of methyl (2R,3R)-2-methyl-3-hydroxybutanoate obtained in Example 1-(5)

Concrete compound names of optically active compounds having plural chiral centers of the first type of the present invention are as shown below.

Optically active 2-chloro-3-hydroxybutanoic acid ester

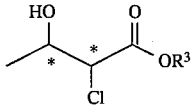

Optically active 2-fluoro-3-hydroxybutanoic acid ester

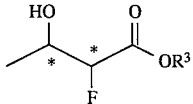

Optically active 2-methyl-3-hydroxy-4-chlorobutanoic acid ester

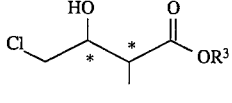

Optically active 2-methyl-3-hydroxy-4-cyanobutanoic acid ester

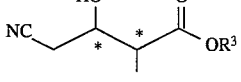

Optically active 2-methyl-3-hydroxy-5-phenyl-4-pentenoic acid ester

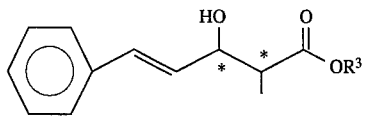

Optically active 2-methyl-3-hydroxy-4-benzyloxybutanoic acid ester

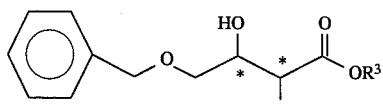

Optically active 2-benzyl-3-hydroxybutanoic acid ester

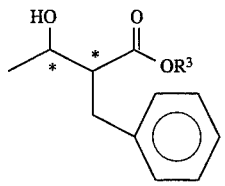

Optically active 2-methyl-3-hydroxy-3-(4-methoxyphenyl)-propanoic acid ester

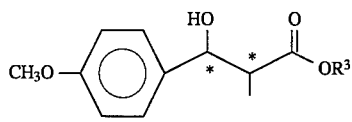

Optically active 2-methyl-3-hydroxy-4-(2-pyridyl)-butanoic acid ester

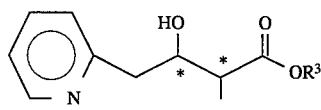

Optically active 2-methyl-3-hydroxy-4-(3-pyridyl)-butanoic acid ester

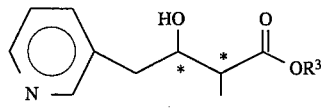

Optically active 2-methyl-3-hydroxy-4-(2-pyrimidyl)-butanoic acid ester

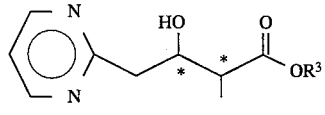

Optically active 2-methyl-3-hydroxy-4-(2-dioxyl)-butanoic acid ester

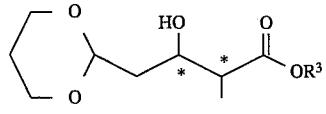

Optically active 2-methyl-3-hydroxy-5-trimethylsilyl-4-pentanoic acid ester

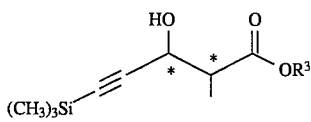

Optically active 2-methyl-3-hydroxy-3-methoxycarbonyl-propanoic acid ester

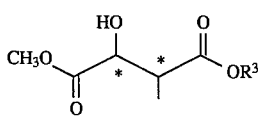

The first type of the process for the production according to the present invention comprises two steps as shown in the following scheme I. That is, (i) resolution by using a hydrolase and (ii) resolution of synform and anti-form by recrystallization of 2,6-cis-1,3-dioxan-4-one form.

Item (i), according to the first type of the process for resolution of the present invention which will be described later, compounds of formula (7-1) and formula (6-1) are obtained by resolution and then, are subjected to hydrolysis or alcoholysis plus hydrolysis to give optically active 2-substituted-3-hydroxy carboxylic acids of formulas (19-a) and (19-b).

The carboxylic acids are reacted with an aldehyde of the following general formula, $$R^4CHO \qquad (22)$$

to produce optically active 2,6-cis-2,5,6-substituted-1,3-dioxan-4-one compounds of formulas (9") and (9').

Recrystallizing the above-mentioned compounds [item (ii) above] results in separation of crystals and mother liquor for recrystallization, and there are obtained 2,5,6-substituted-1,3-dioxan-4-one compounds having the absolute configuration represented by formulas (12) and (14), or (13) and (15). Then the resulting products are subjected to an acetal ring-opening reaction to produce 2-substituted-3-hydroxy-carboxylic acid esters having the absolute configuration represented by formulas (5'), (3'), (4') and (2').

Scheme I

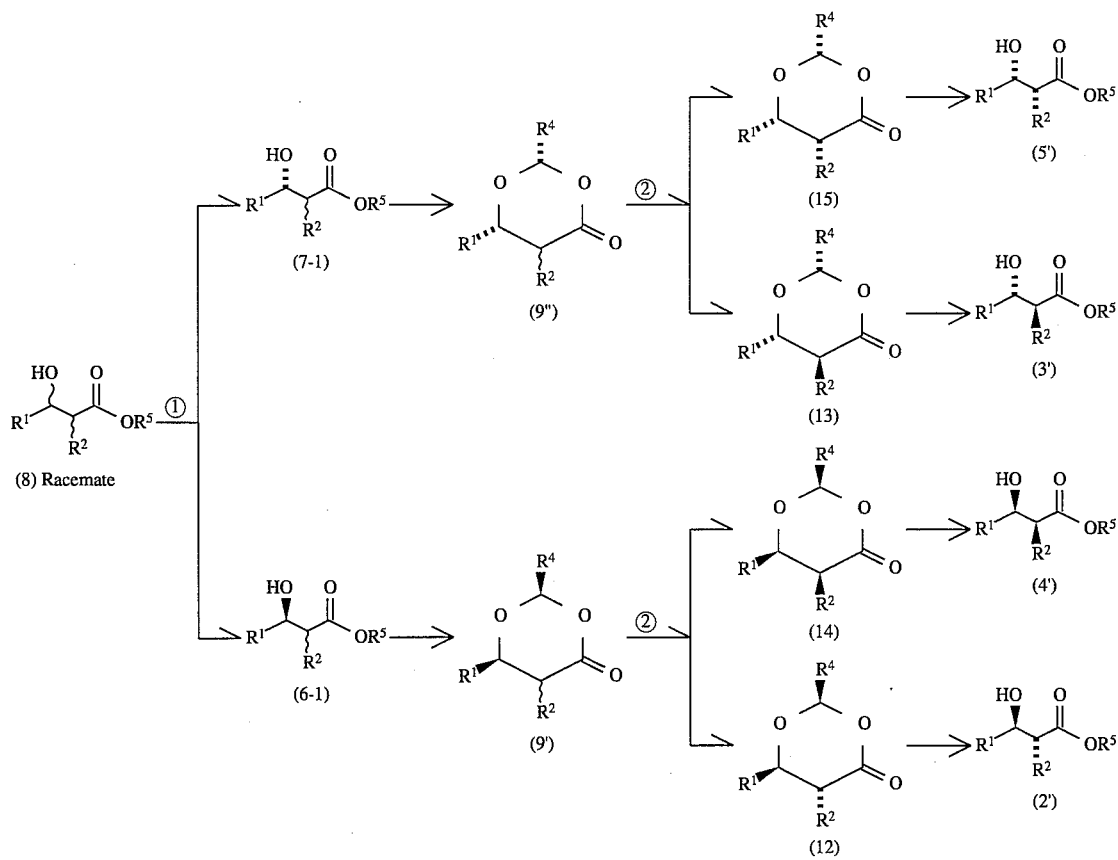

The first type of the process of resolution comprising transesterification using hydrolase is carried out by efficiently contacting a racemate as a substrate, an acylating agent (ester) and a hydrolase with one another under a substantially anhydrous condition. In other words, in a racemate of formula (8), that is, compounds of formula (6-1) and formula (7-1),

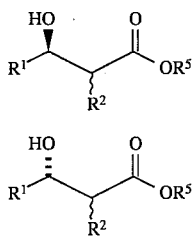

OH group of one of the two compounds is selectively esterified and OH group of the other remains not esterified, and thereby, the compound of formula (8) is resolved into an optically active alcohol and an optically active ester.

The reaction temperature of the transesterification is usually 0°–100° C. and the optimum reaction temperature varies depending on the type of enzyme, but the temperature is preferably 20°–45° C.

The reaction time is usually 5–2000 hours though it varies depending on the type of substrate, but it is possible to shorten the time by varying the reaction temperature, type of enzyme and concentration of substrate.

When the substrate is sparingly soluble in an acylating agent, organic solvents such as toluene, heptane, hexane, diethyl ether and the like can be added without any problem.

The molar ratio of the racemate-alcohol as a substrate to the acylating agent ranges usually from 1:0.5 to 1:2, preferably from 1:1.1 to 1:2.

After completion of the transesterification, the enzyme can be removed from the reaction system by an ordinary filtration procedure and then used again as it is.

The reaction products, a filtrate, can be separated into the optically active alcohol and its enantiomer, the optically active ester, respectively, by vacuum distillation, column chromatography or the like. Further, the resulting optically active ester can be converted to an optically active alcohol which is an enantiomer of the above-mentioned optically active alcohol by hydrolysis.

A substrate used for transesterification is preferably that having 3 carbon atoms or more at the ester moiety. For example, as shown in Examples (infra), the substrate where $R^5$ is isopropyl or t-butyl exhibits higher selectivity and resolution efficiency than the substrate where $R^5$ is methyl or ethyl. Further, the former is also advantageous since it is easy to enhance the optical purity by effecting the enzymatic reaction again even when the optical purity is insufficient.

The second type of the process for resolution according to the present invention can be represented by the following scheme II.

Scheme II

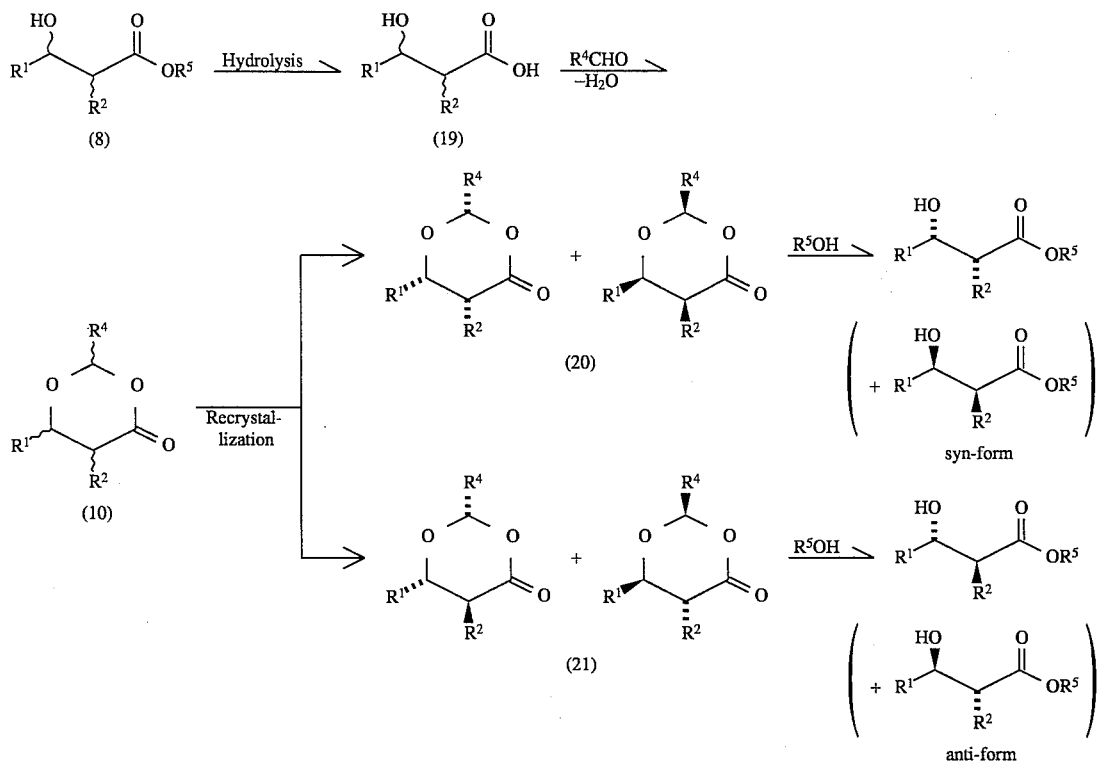

2-Substituted-3-hydroxycarboxylic acid ester (8) is hydrolyzed to give 2-substituted-3-hydroxycarboxylic acid (19). The compound (19) and an aldehyde of the formula, $R^4CHO$, are subjected to dehydration in the presence of an acid catalyst such as p-toluenesulfonic acid pyridium salt, sulfuric acid and the like resulting in forming 1,3-dioxan-4-one compound (10). The compound (10) is subjected to recrystallization and separated into the crystal and a mother liquor, and from the respective ones, the compound of formula (21) and the compound of formula (20) are obtained.

The compounds (20) and (21) thus separated by recrystallization are subjected to an acetal ring-opening reaction in the presence of an acid catalyst such as PPTS, sulfuric acid and the like by using various alcohols to produce syn-form compounds from compounds (20) and anti-form compounds from compounds (21).

When the racemate (8) is used as a starting material, the resulting compounds are syn-form and anti-form compounds, but when the compounds of formula (6-1) and formula (7-1) are used in place of the starting material (8), the resulting products are the compound of formula (2') and the compound of formula (4'), or the compound of formula (3') and the compound of formula (5'), respectively.

Recrystallization used in the process for preparation or the process for resolution may be an ordinary operation for separating crystals and the mother liquor of recrystallization from each other. The operation does not require any particular procedure and apparatus and the like.

Further, it is possible to separate completely by effecting recrystallization once to three times.

As the solvent for recrystallization, any commercially available organic solvent may be used as far as it is capable of separating compounds. However, from the standpoints of ease of recrystallization, solubility, separating ability and the like, preferable solvents include toluene, hexane, heptane, benzene, petroleum ether, ligroin, ethyl acetate, acetone, ethanol, methanol and the like and a mixture thereof.

The 2-substituted-3-hydroxycarboxylic acid ester represented by formula (8) used in the process for preparation and the process for resolution may be easily produced, for example, by the following scheme.

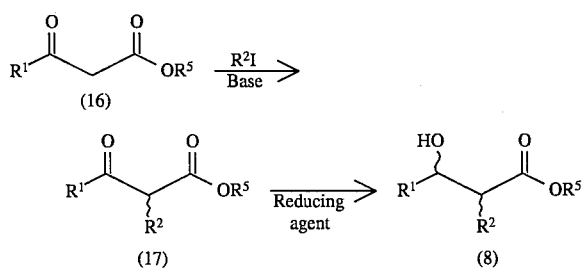

That is, a 3-oxocarboxylic acid ester of formula (16), which is easily commercially available, is reacted with a halide of the formula, $R^2 I$, in the presence of a base such as sodium alcoholate, potassium carbonate, sodium carbonate and the like to produce a 2-substituted-3-oxocarboxylic acid ester (17). The ester (17) is subjected to reduction by using a reducing agent such as sodium borohydride so as to reduce the carbonyl group only and the racemate of formula (8) is produced.

Further, as shown by the following scheme, racemates of the formula (8) can be obtained by reacting various aldehydes with α-bromoalkanoic acid esters of the formula (18) in the presence of metallic zinc,

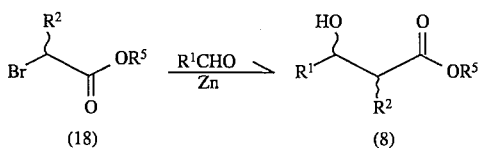

where $R^1$, $R^2$ and $R^5$ are as defined above. Exemplary suitable compounds of formula (8) in the process for preparation and the process for resolution according to the present invention include methyl 2-methyl-3-hydroxybutanoate,
ethyl 2-methyl-3-hydroxybutanoate,
t-butyl 2-methyl-3-hydroxybutanoate,
methyl 2-ethyl-3-hydroxybutanoate,
t-butyl 2-ethyl-3-hydroxybutanoate,
t-butyl 2-propyl-3-hydroxybutanoate,
methyl 2-allyl-3-hydroxybutanoate,
t-butyl 2-allyl-3-hydroxybutanoate,
t-butyl 2-vinyl-3-hydroxybutanoate,
t-butyl 2-acetyl-3-hydroxybutanoate,
t-butyl 2-Phenyl-3-hydroxybutanoate,
t-butyl 2-benzyl-3-hydroxybutanoate,
methyl 2-methyl-3-hydroxypentanoate,
isopropyl 2-methyl-3-hydroxypentanoate,
t-butyl 2-methyl-3-hydroxypentanoate,
t-butyl 2-allyl-3-hydroxypentanoate,
t-butyl 2-phenyl-3-hydroxypentanoate,
methyl 2-chloro-3-hydroxypentanoate,
ethyl 2-chloro-3-hydroxypentanoate,
propyl 2-chloro-3-hydroxypentanoate,
t-butyl 2-chloro-3-hydroxypentanoate,
t-butyl 2-methyl-3-hydroxy-4-chloro-butanoate,
methyl 2-methyl-3-hydroxy-4-pentenoate,
ethyl 2-methyl-3-hydroxy-4-pentenoate,
t-butyl 2-methyl-3-hydroxy-4-pentenoate,
t-butyl 2-vinyl-3-hydroxy-4-pentenoate,
t-butyl 2-allyl-3-hydroxy-4-pentenoate,
methyl 2-methyl-3-hydroxy-4-hexenoate,
ethyl 2-methyl-3-hydroxy-4-hexenoate,
t-butyl 2-methyl-3-hydroxy-4-hexenoate,
t-butyl 2-vinyl-3-hydroxy-4-hexenoate,
t-butyl 2-allyl-3-hydroxy-4-hexenoate,
2-chloro-3-hydroxybutanoic acid ester,
2-fluoro-3-hydroxybutanoic acid ester,
2-methyl-3-hydroxy-4-chlorobutanoic acid ester,
2-methyl-3-hydroxy-4-cyanobutanoic acid ester,
2-methyl-3-hydroxy-5-phenyl-4-pentenoic acid ester,
2-methyl-3-hydroxy-4-benzyloxybutanoic acid ester,
2-benzyl-3-hydroxybutanoic acid ester,
2-methyl-3-hydroxy-4-(4-methoxyphenyl)-propanoic acid ester,
2-methyl-3-hydroxy-4-(2-pyridyl)-butanoic acid ester,
2-methyl-3-hydroxy-4-(3-pyridyl)-butanoic acid ester,
2-methyl-3-hydroxy-4-(3-pyrimidyl)-butanoic acid ester,
2-methyl-3-hydroxy-4-(2-dioxyl)-butanoic acid ester,
2-methyl-3-hydroxy-5-trimethylsilyl-4-pentynoic acid ester,
and
2-methyl-3-hydroxy-3-methoxycarbonylpropanoic acid ester.

As hydrolases used in the process for preparation and the process for resolution according to the present invention, lipase, lipoprotein lipase, esterase and the like are particularly preferable.

However, any hydrolase may be used which can act on a racemate of the formula (8) and cause preferentially a transesterification reaction with either of (3R) form and (3S) form.

For example, commercially available enzymes are as shown in the following table.

| Trade name | Origin | Seller or Maker |
| --- | --- | --- |
| Lipase AP | Aspergillus niger | Amano Pharmaceutical Co., Ltd. |
| Lipase M | Mucor javanicus | Amano Pharmaceutical Co., Ltd. |
| Lipase P | Pseudomonas fluorescens | Amano Pharmaceutical Co., Ltd. |
| Lipase CES | Pseudomonas sp | Amano Pharmaceutical Co., Ltd. |
| Lipase CE | Humicola lanuginosa | Amano Pharmaceutical Co., Ltd. |
| Lipase F-AP | Rhizopus javanicus | Amano Pharmaceutical Co., Ltd. |
| Lipase II | Porcine Pancreas | Sigma Chemical Co. |
| Lipase VIII | Geotrichum Candidum | " |
| Lipase X | Rhizopus delamar | " |
| Lipase | Chromobacterium Viscosum | Toyo Jozo Co., Ltd. |
| Lipase A | Aspergillus niger | Novo Industi A/S |
| Lipase | Rhizopus niveus | Nagase, Biochemicals, Ltd. |
| Lipase B | Pseudomonas fragi | Sapporo Beer Co. |

Other than the above-mentioned enzyme, any microorganisms producing a hydrolase capable of effecting the transesterification may be used for taking out the hydrolase.

Examples of such microorganisms include the following genuses: Arthrobacter, Acromobacter, Alcaligenes, Aspergillus, Chromobacterium, Candida, Mucor, Pseudomonas, and Rhizopus. Among them, Pseudomonas genus is particularly preferable.

As esters used for the preparation and resolution according to the present invention, easily available commercial products are satisfactorily used. Such esters include methyl propionate, ethyl butyrate, ethyl stearate, trichloroethyl laurate, butyl laurate, ethylene glycol diacetate and the like. In particular, vinyl esters and triglycerides are preferable and they are, for example, vinyl acetate, vinyl caproate, vinyl laurate, triacetin, tripropionin, tributyrin, tricaproin, tristearin, trilaurin, trimyristin, and triolein.

As aldehydes of the formula $R^4CHO$ according to the process for preparation of the present invention, there may be mentioned acetaldehyde, propionaldehyde, butyraldehyde, valeraldehyde, benzaldehyde, pivalaldehyde, and chloral.

According to the preparation of the present invention, it is preferred that the 1,3-dioxan-4-one compound of the formula (9) or (10) obtained by the reaction with aldehyde has a high melting point and exhibits good recrystallization, and therefore, pivalaldehyde and chloral are preferable.

As alcohols used for acetal ring-opening reaction in the preparation or resolution according to the present invention, there may be used alkyl alcohols, alkenyl alcohols, alkynyl alcohols and the like. Desired optically active compounds of the present invention can be produced by selecting appropriate alcohols.

The compounds of the present invention can be converted to various useful compounds due to the plural chiral centers.

The optically active compounds having plural chiral centers represented by the formulas (1), (11) and the like of the present invention can be easily converted to β-lactam compounds through acid amide compounds. The β-lactam compounds can be starting materials for producing carbapenem compounds, antibiotics which particularly draw people's attention. For example, as shown in the following scheme, β-lactam compounds derived from the compounds of the present invention can be easily converted to the desired carbapenem compounds since $R^1$ and $R^2$ in the following formula can be optionally converted.

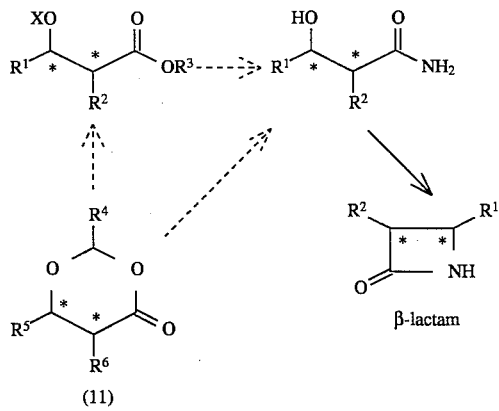

(11)

According to the present invention, the following advantages can be attained at least partly.

(i) Since the transesterification can be effected under substantially anhydrous condition, unnecessary hydrolysis of esters scarcely occurs.

(ii) Recovery and reuse of enzymes can be effected easily.

(iii) The reaction is effected at relatively low temperatures and at an open system, and therefore, a particular apparatus and material are not necessary.

(iv) The optically active compound of high purity can be obtained by a one-step reaction.

(v) Buffer solutions and the like are not necessary and therefore, despite biochemical reactions, the substrate concentration can be high and reactors of a large volume as compared with that of the substrate are not necessary.

(vi) When the 1,3-dioxan-4-one compound derived from the 2-substituted-3-substituted-carboxylic acid compound is resolved into syn-form and anti-form by recrystallization, efficiency of recrystallization is very high and the resolution of syn-form and anti-form can be accomplished by effecting recrystallization once to three times.

(vii) Desired esters can be easily produced by a ring-opening reaction of the optically active 1,3-dioxan-4-one compound caused by the action of various alcohols corresponding to said desired esters.

(viii) Among the compounds of formula (1) obtained by the preparation of the present invention, compounds where $R^3$ is t-butyl have a high stability at the ester moiety and this fact is advantageous upon converting the compounds to various other compounds.

The invention is now more particularly described with reference to the following examples which are for the purpose of illustration only and are intended to imply no limitation thereon.

EXAMPLE 1

Optical resolution of t-butyl 2-methyl-3-hydroxybutanoate ( $R^1=R^2=$—$CH_3$, $R^5=$—$C(CH_3)_3$ in formula (8))

(1) A mixture of a racemate, t-butyl 2-methyl-3-hydroxybutanoate 30 g, vinyl laurate 40 g, and Lipase P (Amano Pharmaceutical Co., Ltd. ) 8.0 g was stirred at 35° C. for 7 days.

After stopping the reaction, the enzyme was removed by filtration and washed with n-heptane on a filter paper. n-Heptane was distilled off from the filtrate and the residue was subjected to a vacuum distillation to give 13 g of t-butyl (3S)-2-methyl-3-hydroxybutanoate of the following formula,

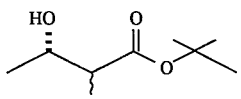

and 23 g of t-butyl (3R)-2-methyl-3-dodecanoyloxy butanoate of the following formula,

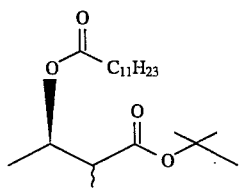

(2) A mixture of t-butyl (3R)-2-methyl-3-dodecanoyloxybutanoate obtained in (1) above 23 g, methanol 60 ml, and concentrated sulfuric acid 1.0 ml was refluxed for 30 hours, and 100 ml of water was added followed by extraction with ether. The ether layer was dried with anhydrous sodium sulfate, and the ether was distilled off and the residue was subjected to vacuum distillation to give 5.1 g of methyl (3R)-2-methyl-3-hydroxybutanoate. b.p. 62°–65° C. (6.0 mm Hg)

$[\alpha]_D^{30}$=−24.4°(C=1.27, $CHCl_3$)

A mixture of the methyl (3R)-2-methyl-3-hydroxybutanoate 4.7 g and a 20% sodium hydroxide 15 ml was stirred for one hour at room temperature, and a concentrated hydrochloric was gradually added thereto to acidify the mixture followed by ether extraction. The ether layer was dried over anhydrous sodium sulfate and the ether was distilled to obtain 3.6 g of (3R)-2-methyl-3-hydroxybutanoic acid.

(3) A mixture of (3R)-2-methyl-3-hydroxybutanoic acid 3.6 g, chloral 8.3 g, pyridinium p-toluenesulfonate (PPTS) 0.7 g and dichloromethane 20 ml was refluxed for 25 hours under a dehydration condition. 40 ml of a saturated aqueous sodium hydrogen carbonate was added thereto and the resulting separated organic phase was dried over anhydrous magnesium sulfate and the solvent was distilled off to obtain 6.3 g of (2R, 6R)-2-trichloro-methyl-5,6-dimethyl-1,3-dioxan-4-one.

(4) 6.3 g of (2R, 6R)-2-trichloromethyl-5,6-dimethyl-1, 3-dioxan -4-one obtained in (3) above was recrystallized from 45 ml of n-heptane and filtered, and 1.1 g of (2R, 5R, 6R)-2-trichloromethyl-5,6-dimethyl-1,3-dioxan.-4one of the following formula was obtained from the filter cake.

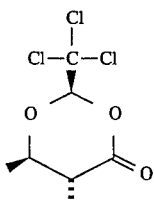

m.p. 128.4°–130.4° C.

Figure 5:
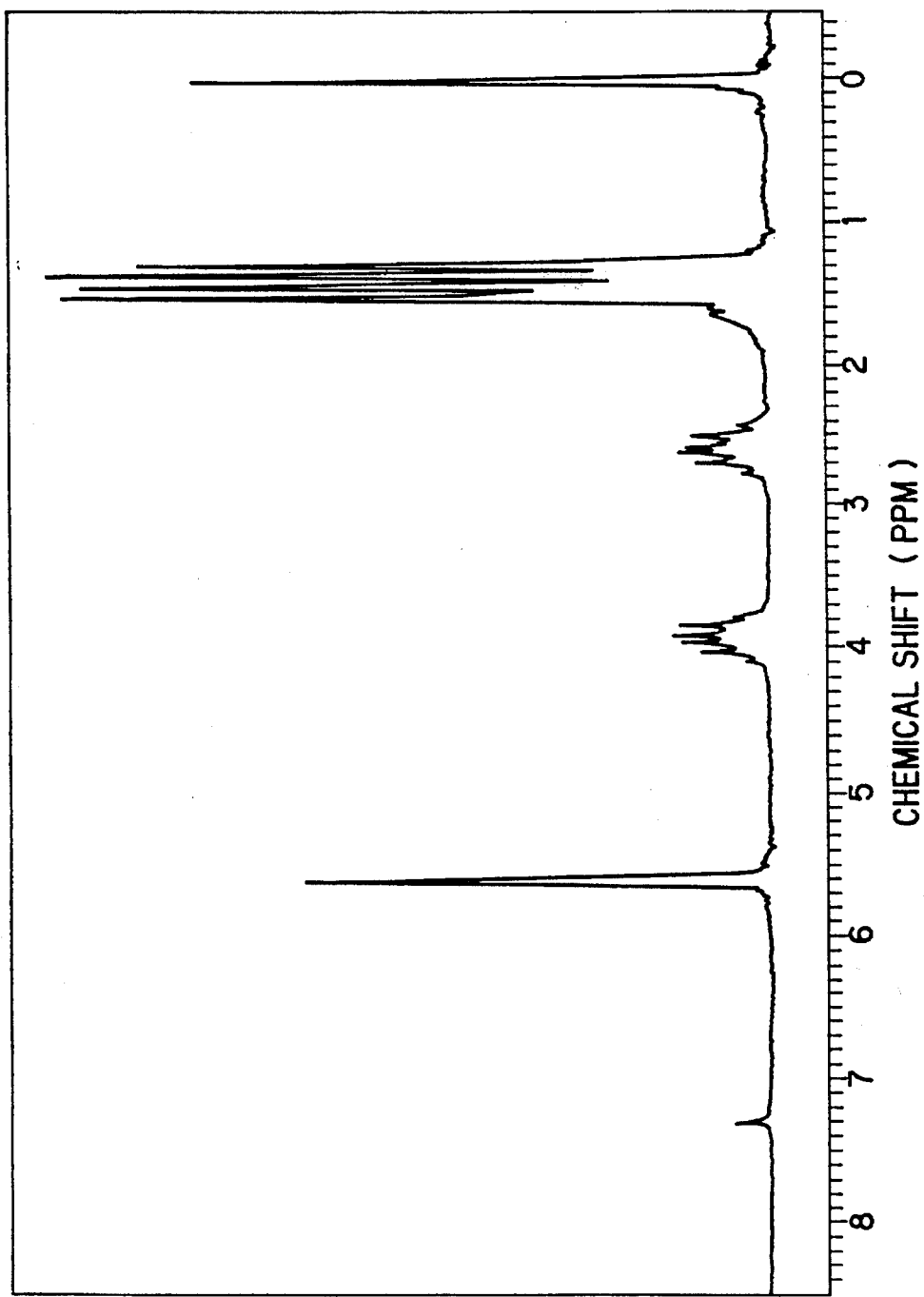
FIG. 5 shows an NMR spectrum of (2R,5R,6R)-2-trichloro-methyl-5,6-dimethyl-1,3-dioxan-4-one obtained in Example 1-(4)

$[\alpha]_D^{31} = -27.2°$ (C=1.00, CHCl$_3$) The corresponding NMR chart is shown in FIG. 5. From the filtrate 0.6 g of (2R, 5S, 6R)-2-trichloromethyl-5,6-dimethyl-1,3-dioxan-4-one of the following formula was obtained.

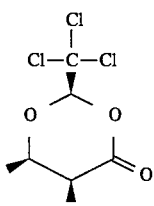

(5) A mixture of 1.1 g of (2R,5R,6R)-2-trichloro-methyl-5,6-dimethyl-1,3-dioxan-4-one obtained in (4), 10 ml of methanol and 0.1 ml of concentrated sulfuric acid was stirred at room temperature for one hour and 20 ml of water was added followed by ether extraction. The ether phase was dried over sodium sulfate, and ether was distilled off and the residue was subjected to vacuum distillation to give 0.5 g of methyl (2R,3R)-2-methyl-3-hydroxybutanoate.

$[\alpha]_D^{30} = -28.8°$ (C=1.12, CHCl$_3$)

The optical purity of the resulting methyl (2R,3R)-2-methyl-3-hydroxybutanoate was determined by the following procedure.

A mixture of methyl (2R,3R)-2-methyl-3-hydroxybutanoate 0.3 g, R-(+)-methoxytrifluoromethylphenyl acetic acid [(+)-MTPA] 0.53 g, dicyclohexylcarbodiimide 0.47 g and dichloromethane 7 ml was stirred at room temperature for one hour, and the resulting crystal was filtered and dichloromethane was distilled off.

The resulting residue was subjected to column chromatography (silica gel, solvent : n-heptane, ethyl acetate 9:1) for purification, and there was obtained (+)-MTPA ester of methyl (2R,3R)-2-methyl-3-hydroxybutanoate, which was then measured by $^1$H-NMR of 270 MHz.

Figure 2:
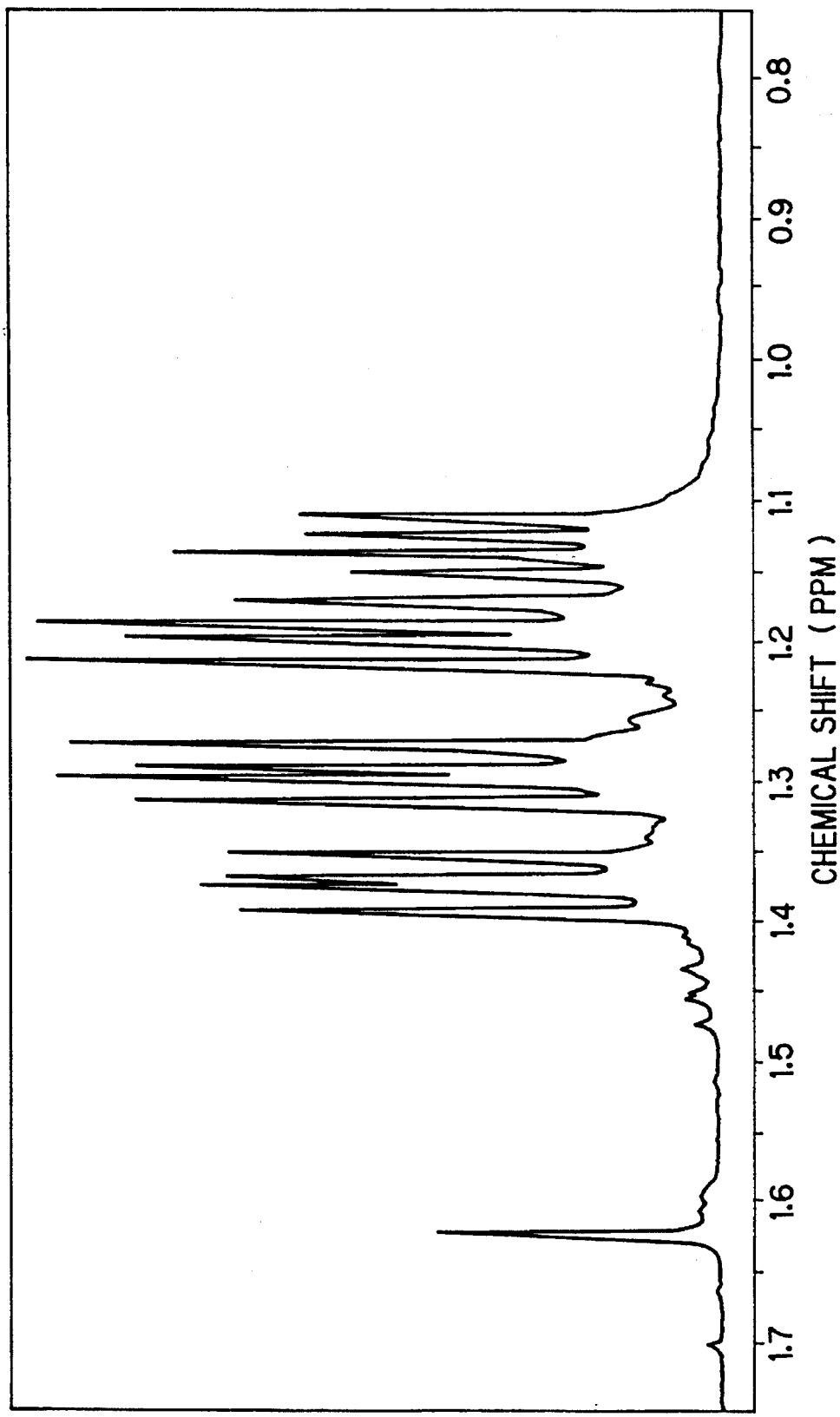
FIG. 2 shows a $^1$H-NMR spectrum of (+)-MTPA ester of the racemate of methyl 2-methyl-3-hydroxybutanoate.

The result is shown in FIG. 1. Peaks due to enantiomer are hardly found and this fact shows that this product is optically pure. For comparison, $^1$H-NMR of the racemate, (+)-MTPA ester, is shown in FIG. 2.

(6) 0.6 g of (2R,5S,6R)-2-trichloromethyl-5,6-dimethyl-1,3-dioxan-4-one obtained in (4) was subjected to a ring-opening reaction in a methanol-concentrated sulfuric acid in a manner similar to the procedure in (5) above, to give 0.3 g of methyl (2S,3R)-2-methyl-3-hydroxybutanoate.

(7) From 10 g of t-butyl (3S)-2-methyl-3-hydroxybutanoate obtained in (1), the following products were obtained by the methods similar to (2),(3) and (4).

(2S, 5S, 6S)-2-trichloromethyl-5,6-dimethyl-1,3-dioxan-4-one of the formula,

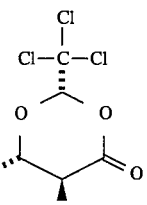

3.1 g [m.p. 122.6°–130.2° C, $[\alpha]_D^{30} = +23.0°$ (C=1.31, CHCl$_3$)] and 2.2 g of (2S, 5R, 6S)-2-trichloromethyl-5,6-dimethyl-1,3-dioxan-4-one of the formula,

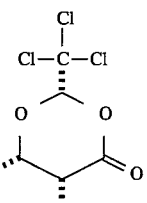

(8) These products were subjected to acetal ring opening by using a methanol-concentrated sulfuric acid system to produce methyl(2S, 3S)-2-methyl-3-hydroxybutanoate [[$\alpha$]$_D^{29}$=+27.5° (C=1.09, CHCl$_3$)], 1.1 g and methyl (2R, 3S)-2-methyl-3-hydroxybutanoate, 0.9 g.

EXAMPLE 2

Figure 6:
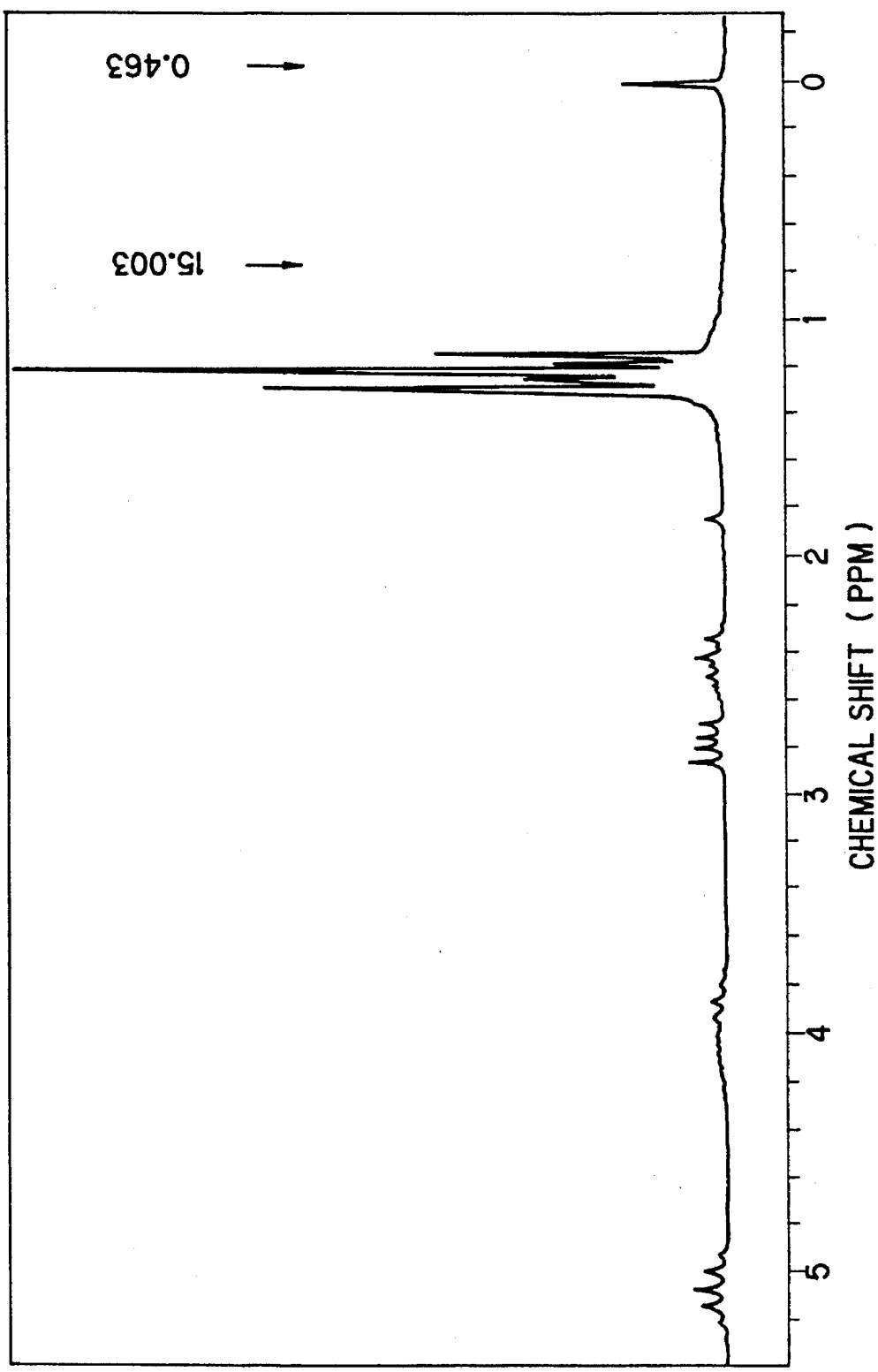
FIG. 6 shows an NMR spectrum of isopropyl (2R,3R)-2-methyl-3-hydroxybutanoate obtained in Example 2-(1)

(1) To 1.0 g of (2R, 5R, 6R)-2-trichloromethyl-5,6-dimethyl-1,3-dioxan-4-one obtained by procedures similar to (1)–(4) of Example 1 were added 0.1 ml of concentrated sulfuric acid and 10 ml of 2-propanol and stirred at room temperature for one hour, and 20 ml of water was added to effect ether extraction. After drying the ether phase over anhydrous sodium sulfate, the ether was distilled off and the residue was subjected to distillation to give 0.4 g of isopropyl (2R, 3R)-2-methyl-3-hydroxybutanoate. The NMR chart is shown in FIG. 6.

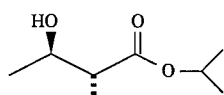

(2) Repeating the procedure of Example 2-(1) except that 2-propanol was replaced with 2-butanol, 0.5 g of 1-methylpropyl (2R, 3R)-2-methyl-3-hydroxybutanoate of the following formula was obtained.

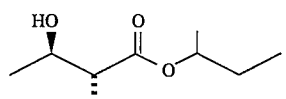

(3) Repeating the procedure of Example 2 - (1) except that 2-propanol was replaced with 1-propanol, 0.5 g of propyl (2R, 3R)-2-methyl-3-hydroxybutanoate of the following formula was obtained.

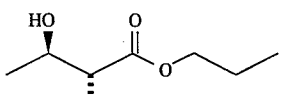

(4) Repeating the procedure of Example 2- (1) except that 2-propanol was replaced with 1-butanol, 0.5 g of butyl (2R, 3R)-2-methyl-3-hydroxybutanoate of the following formula was obtained.

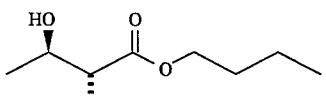

(5) Repeating the procedure of Example 2-(1) except that 2-propanol was replaced with 1-pentanol, 0.5 g of pentyl (2R, 3R)-2-methyl-3-hydroxybutanoate of the following formula was obtained.

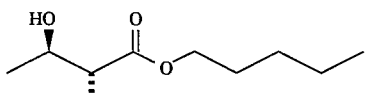

(6) Repeating the procedure of Example 2-(1) except that 2-propanol was replaced with 1-hexanol, 0.5 g of hexyl (2R, 3R)-2-methyl-3-hydroxybutanoate of the following formula was obtained.

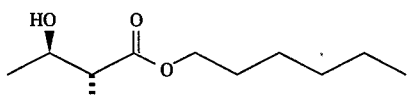

Figure 7:
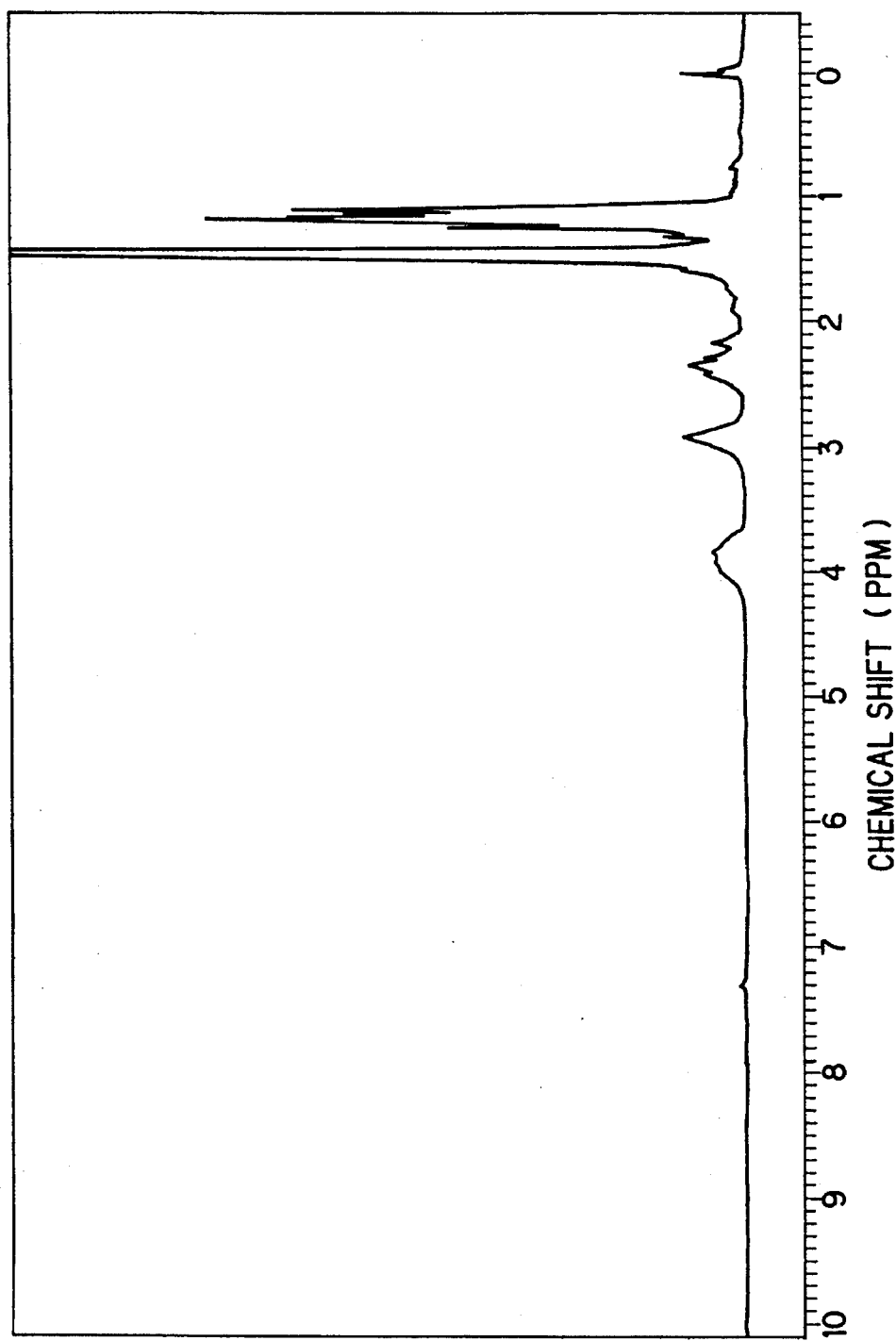
FIG. 7 shows an NMR spectrum of t-butyl (2R,3R)-2-methyl-3-hydroxybutanoate obtained in Example 2-(7)

(7) Repeating the procedure of Example 2-(1) except that 2-propanol was replaced with t-butanol, 0.5 g of t-butyl (2R, 3R)-2-methyl-3-hydroxybutanoate of the following formula was obtained. The NMR chart was shown in FIG. 7.

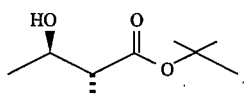

(8) Repeating the procedure of Example 2-(1) except that 2-propanol was replaced with allyl alcohol, 0.5 g of allyl (2R, 3R)-2-methyl-3-hydroxybutanoate of the following formula was obtained.

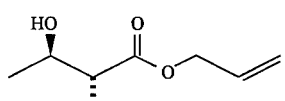

(9) Repeating the procedure of Example 2-(1) except that 2-propanol was replaced with benzyl alcohol, 0.6 g of benzyl (2R, 3R)-2-methyl-3-hydroxybutanoate of the following formula was obtained.

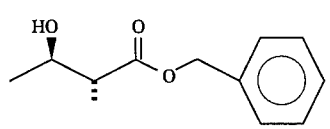

(10) Repeating the procedure of Example 2-(1) except that 2-propanol was replaced with vinyl alcohol, 0.4 g of vinyl (2R, 3R)-2-methyl-3-hydroxybutanoate of the following formula was obtained.

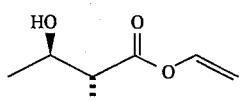

EXAMPLE 3

(1) TO 1.0 g of (2R, 5S, 6R)-2-trichloromethyl-5,6-dimethyl-1,3-dioxan-4-one obtained by a procedure similar to Example 1-(4) were added 0.1 ml of concentrated sulfuric acid and 10 ml of 2-propanol, stirred at room temperature for one hour, and 20 ml of water was added followed by ether extraction. The ether phase was dried over anhydrous sodium sulfate and ether was distilled off, and then the residue was subjected to distillation to obtain 0.4 g of isopropyl (2S, 3R)-2-methyl-3-hydroxybutanoate.

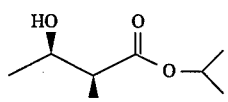

(2) Repeating the procedure of Example 3- (1) except that 2-propanol was replaced with 2-butanol, 0.5 g of 1-methylpropyl ( 2S, 3R ) -2-methyl-3-hydroxybutanoate of the following formula was obtained.

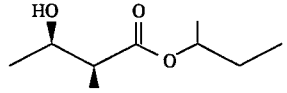

(3) Repeating the procedure of Example 3-(1) except that 2-propanol was replaced with 1-propanol, 0.5 g of propyl (2S, 3R)-2-methyl-3-hydroxybutanoate of the following formula was obtained.

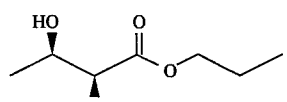

(4) Repeating the procedure of Example 3-(1) except that 2-propanol was replaced with 1-butanol, 0.5 g of butyl (2S, 3R)-2-methyl-3-hydroxybutanoate of the following formula was obtained.

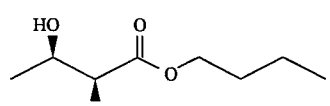

(5) Repeating the procedure of Example 3-(1) except that 2-propanol was replaced with 1-pentanol, 0.5 g of pentyl (2S, 3R)-2-methyl-3-hydroxybutanoate of the following formula was obtained.

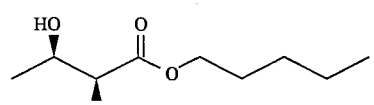

(6) Repeating the procedure of Example 3-(1) except that 2-propanol was replaced with 1-hexanol, 0.5 g of hexyl (2S, 3R)-2-methyl-3-hydroxybutanoate of the following formula was obtained.

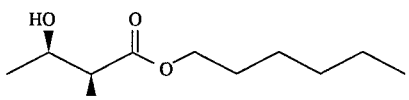

(7) Repeating the procedure of Example 3-(1) except that 2-propanol was replaced with t-butanol, 0.5 g of t-butyl (2S, 3R)-2-methyl-3-hydroxybutanoate of the following formula was obtained.

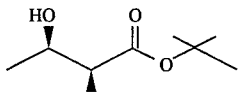

(8) Repeating the procedure of Example 3-(1) except that 2-propanol was replaced with allyl alcohol, 0.5 g of allyl (2S, 3R)-2-methyl-3-hydroxybutanoate of the following formula was obtained.

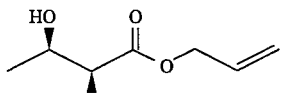

(9) Repeating the procedure of Example 3-(1) except that 2-propanol was replaced with benzyl alcohol, 0.6 g of benzyl (2S, 3R)-2-methyl-3-hydroxybutanoate of the following formula was obtained.

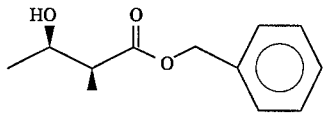

(10) Repeating the procedure of Example 3-(1) except that 2-propanol was replaced with vinyl alcohol, 0.4 g of vinyl (2S, 3R)-2-methyl-3-hydroxybutanoate of the following formula was obtained.

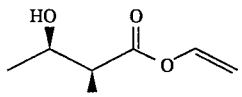

EXAMPLE 4

(1) TO 1.0 g Of (2S, 5S, 6S)-2-trichloromethyl-5,6-dimethyl-1,3-dioxan-4-one obtained by a procedure similar to Example 1-(7) were added 0.1 ml of concentrated sulfuric acid and 10 ml of 2-propanol, stirred at room temperature for one hour, and 20 ml of water was added followed by ether extraction.

The ether phase was dried over anhydrous sodium sulfate and the residue was subjected to distillation to give 0.4 g of isopropyl (2S, 3S)-2-methyl-3-hydroxybutanoate of the following formula.

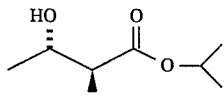

(2) Repeating the procedure of Example 4-(1) except that 2-propanol was replaced with 2-butanol, 0.5 g of 1-methyl-propyl (2S, 3S)-2-methyl-3-hydroxybutanoate of the following formula was obtained.

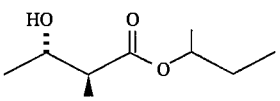

(3) Repeating the procedure of Example 4-(1) except that 2-propanol was replaced with 1-propanol, 0.5 g of propyl (2S, 3S)-2-methyl-3-hydroxybutanoate of the following formula was obtained.

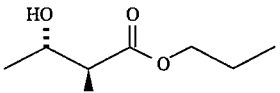

(4) Repeating the procedure of Example 4-(1) except that 2-propanol was replaced with 1-butanol, 0.5 g of butyl (2S, 3S)-2-methyl-3-hydroxybutanoate of the following formula was obtained.

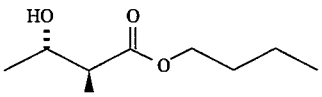

(5) Repeating the procedure of Example 4-(1) except that 2-propanol was replaced with 1-pentanol, 0.5 g of pentyl (2S, 3S)-2-methyl-3-hydroxybutanoate of the following formula was obtained.

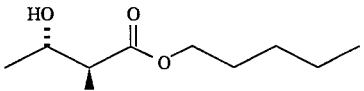

(6) Repeating the procedure of Example 4-(1) except that 2-propanol was replaced with 1-hexanol, 0.5 g of hexyl (2S, 3S)-2-methyl-3-hydroxybutanoate of the following formula was obtained.

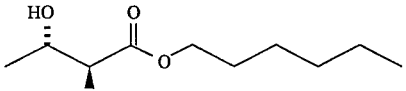

(7) Repeating the procedure of Example 4-(1) except that 2-propanol was replaced with t-butanol, 0.5 g of t-butyl (2S, 3S)-2-methyl-3-hydroxybutanoate of the following formula was obtained.

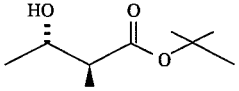

(8) Repeating the procedure of Example 4-(1) except that 2-propanol was replaced with allyl alcohol, 0.5 g of allyl (2S, 3S)-2-methyl-3-hydroxybutanoate of the following formula was obtained.

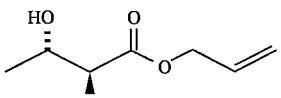

(9) Repeating the procedure of Example 4-(1) except that 2-propanol was replaced with benzyl alcohol, 0.6 g of benzyl (2S, 3S)-2-methyl-3-hydroxybutanoate of the following formula was obtained.

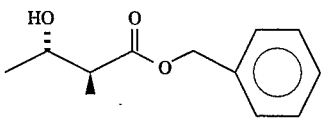

(10) Repeating the procedure of Example 4-(1) except that 2-propanol was replaced with vinyl alcohol, 0.4 g of vinyl (2S, 3S)-2-methyl-3-hydroxybutanoate of the following formula was obtained.

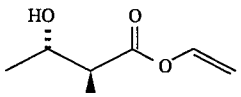

EXAMPLE 5

(1) To 1.0 g of (2S, 5S,6S)-2-trichloromethyl-5,6-dimethyl-1,3-dioxan-4-one produced by a procedure similar to Example 1-(7) were added 0.1 ml of concentrated sulfuric acid and 10 ml of 2-propanol, stirred at room temperature for one hour, and 20 ml of water was added to effect ether extraction.

The ether phase was dried over anhydrous sodium sulfate and ether was distilled off followed by distilling the residue to obtain 0.4 g of isopropyl (2R, 3S)-2-methyl-3-hydroxybutanoate of the following formula.

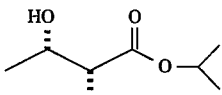

(2) Repeating the procedure of Example 5-(1) except that 2-propanol was replaced with 2-butanol, 0.5 g of 1-methylpropyl (2R, 3S)-2-methyl-3-hydroxybutanoate of the following formula was obtained.

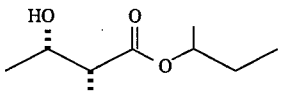

(3) Repeating the procedure of Example 5-(1) except that 2-propanol was replaced with 1-propanol, 0.5 g of propyl (2R,3S)-2-methyl-3-hydroxybutanoate of the following formula was obtained.

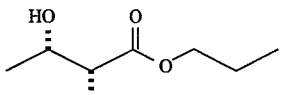

(4) Repeating the procedure of Example 5- (1) except that 2-propanol was replaced with 1-butanol, 0.5 g of butyl (2R, 3S)-2-methyl-3-hydroxybutanoate of the following formula was obtained.

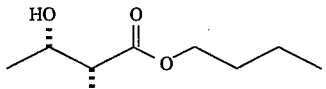

(5) Repeating the procedure of Example 5-(1) except that 2-propanol was replaced with 1-pentanol, 0.5 g of pentyl (2R, 3S)-2-methyl-3-hydroxybutanoate of the following formula was obtained.

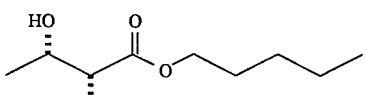

(6) Repeating the procedure of Example 5-(1) except that 2-propanol was replaced with 1-hexanol, 0.5 g of hexyl (2R, 3S)-2-methyl-3-hydroxybutanoate of the following formula was obtained.

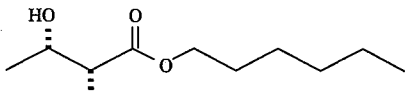

(7) Repeating the procedure of Example 5-(1) except that 2-propanol was replaced with t-butanol, 0.5 g of t-butyl (2R, 3S)-2-methyl-3-hydroxybutanoate of the following formula was obtained.

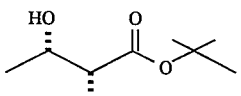

(8) Repeating the procedure of Example 5-(1) except that 2-propanol was replaced with allyl alcohol, 0.5 g of allyl (2R, 3S)-2-methyl-3-hydroxybutanoate of the following formula was obtained.

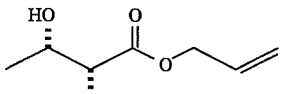

(9) Repeating the procedure of Example 5-(1) except that 2-propanol was replaced with benzyl alcohol, 0.6 g of benzyl (2R, 3S)-2-methyl-3-hydroxybutanoate of the following formula was obtained.

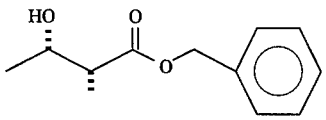

(10) Repeating the procedure of Example 5-(1) except that 2-propanol was replaced with vinyl alcohol, 0.4 g of vinyl (2R, 3S)-2-methyl-3-hydroxybutanoate of the following formula was obtained.

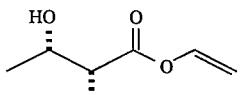

EXAMPLE 6

Optical resolution of methyl 2-methyl-3-hydroxybutanoate [$R^1=R^2=R^5$ =—$CH_3$ in formula (8)]

(1) A mixture of 84 g of methyl 2-methyl-3-hydroxybutanoate as racemate and 1 l. of 20% sodium hydroxide was stirred at room temperature for one hour and then concentrated hydrochloric acid was gradually added thereto to acidify and ether extraction was effected. The ether phase was dried over anhydrous sodium sulfate and ether was distilled off to obtain 74 g of 2-methyl-3-hydroxybutanoic acid.

A mixture of 74 g of the resulting 2-methyl-3-hydroxybutanoic acid, 204 g of chloral, 18 g of PPTS, and 480 ml of dichloromethane was refluxed under dehydration conditions for 30 hours.

To the mixture thus treated was added 1 l. of a saturated aqueous sodium hydrogen carbonate, and the resulting organic phase was separated and dried over anhydrous magnesium sulfate, and then the solvent was distilled off to obtain, as a residue, 2-trichloromethyl-5,6-dimethyl-1,3-dioxan-4-one.

The residue was recrystallized from n-heptane 300 ml and toluene 150 ml and filtered to separate 43.7 g of the resulting crystal.

Then the solvent was distilled away from the filtrate and 27.3 g of residue was obtained.

As shown in (2) and (3) below, it was found that the crystal contained 5,6-anti-2-trichloromethyl-5,6-dimethyl-1,3-dioxan-4-one and the filtrate 5,6-syn-2-trichloromethyl-5,6-dimethyl-1,3-dioxan-4-one.

(2) A mixture of 20 g of crystal obtained in (1) above, 100 ml of methanol, and 1 ml of concentrated sulfuric acid was stirred at room temperature for one hour, and 200 ml of water was added thereto followed by ether extraction.

The resulting ether phase was dried over anhydrous sodium sulfate and ether was distilled away. The residue was subjected to vacuum distillation to give methyl 2,3-anti-2-methyl-3-hydroxybutanoate, b.p. 53° C. (3.5 mm Hg), 11.4 g was obtained.

A mixture of 11.4 g of methyl 2,3-anti-2-methyl-3-hydroxybutanoate, 11.7 g of vinyl laurate, and 5.0 g of Lipase P was stirred at 35° C. for two days. After stopping the reaction, the enzyme was removed by filtration and the enzyme thus removed was washed with n-heptane on a filter paper.

n-Heptane was distilled away from the filtrate to give 5.1 g of methyl (2S, 3S)-2-methyl-3-hydroxybutanoate [b.p. 48.0°–49.5° C./7.0 mm Hg, $[\alpha]_D^{30}=+11.7°$ (C=1.23, CHCl$_3$)] and 11.0 g of methyl (2R, 3R)-2-methyl-3-dodecanoyloxybutanoate as residue.

The product was subjected to alcoholysis in a manner similar to the procedure of Example 1-(2) and converted to methyl (2R, 3R)-2-methyl-3-hydroxybutanoate (4.5 g), $[\alpha]_D^{34}=-24.1°$ (C=1.20, CHCl$_3$).

(3) 20 g of the filtrate obtained in (1) above was subjected to an enzymatic reaction similar to (2) above to produce 4.2 g of methyl (2S, 3R)-2-methyl-3-hydroxybutanoate and 5.3 g of methyl (2R, 3S)-2-methyl-3-hydroxybutanoate.

EXAMPLE 7

Optical resolution of ethyl 2-methyl-3-hydroxybutanoate [$R^1=R^2=$—CH$_3$, $R^5=$—CH$_2$CH$_3$ in formula (8)]

(1) A mixture of 15.0 g of ethyl 2-methyl-3-hydroxybutanoate as racemate, 14.4 g of vinyl laurate, and 12.7 g of Lipase P (trade name, supplied by Amano Pharmaceutical Co., Ltd.) was stirred at 35° C. for seven days. After stopping the reaction, the enzyme was removed and washed with n-heptane on a filter paper.

n-Heptane was distilled away from the filtrate and the residue was subjected to vacuum distillation to give 7.0 g of ethyl (3S)-2-methyl-3-hydroxybutanoate of the following formula, b.p. 66°–67° C. (6.5 mm Hg), $[\alpha]_D^{27}=+12.8°$ (C=1.12, CHCl$_3$).

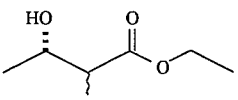

In addition, 5.0 g of ethyl (3R)-2-methyl-3-dodecanoyloxybutanoate was obtained. The resulting (3S) form was converted to (+)-MTPA ester according to a procedure similar to Example 1-(2),(5), and the optical purity determined by $^1$H-NMR was 64% ee.

(2) A mixture of 5.0 g of ethyl (3R)-2-methyl-3-dodecanoyloxybutanoate, 50 ml of methanol; and 0.5 ml of concentrated sulfuric acid was refluxed for 20 hours and 50 ml of water was added thereto followed by ether extraction.

The ether phase was dried over anhydrous sodium sulfate, and ether was distilled away and then the residue was distilled to give 1.1 g of methyl (3R)-2-methyl-3-hydroxybutanoate of the following formula.

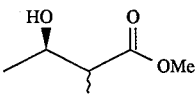

This compound was converted to (+)-MTPA ester according to a method similar to Example 1-(5) and the optical purity determined by $^1$H-NMR was 77% ee.

EXAMPLE 8

Optical resolution of isopropyl 2-methyl-3-hydroxybutanoate [$R^1=R^2=$—CH$_3$, $R^5=$—CH(CH$_3$)$_2$ in formula (8)]

(1) A mixture of 14.0 g of isopropyl 2-methyl-3-hydroxybutanoate as racemate, 9.95 g of vinyl laurate and 8.8 g of Lipase P (trade name, supplied by Amano Pharmaceutical Co., Ltd.) was stirred for six days at 35° C. After stopping the reaction, the enzyme was removed by filtration and washed with n-heptane on a filter paper.

n-Heptane was distilled away from the filtrate and the residue was subjected to vacuum distillation to obtain 8.5 g of isopropyl (3S)-2-methyl-3-hydroxybutanoate of the following formula, b.p. 78° C. (6 mm Hg), $[\alpha]_D^{28}=+9.0°$ (C=1.20, CHCl$_3$).

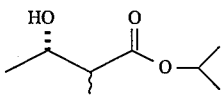

In addition, 12.5 g of isopropyl (3R)-2-methyl-3-dodecanoyloxybutanoate was obtained.

The resulting (3S) form was converted to (+)-MTPA ester according to a procedure similar to Example 1-(2),(5) and the optical purity determined by $^1$H-NMR was 40% ee.

(2) A mixture of 12.5 g of isopropyl (3R)-2-methyl-3-dodecanoyloxybutanoate obtained in (1) above, 100 ml of methanol, and 1 ml of concentrated sulfuric acid was refluxed for 40 hours and 100 ml of water was added thereto followed by ether extraction.

The ether phase was dried over anhydrous sodium sulfate and ether was distilled away, and the residue was distilled to give 1.6 g of methyl (3R)-2-methyl-3-hydroxybutanoate of the following formula, b.p. 61° C. (14 mm Hg).

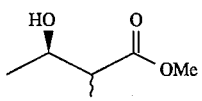

This compound was converted to (+)-MTPA ester according to Example 1-(5) and the optical purity determined by $^1$H-NMR was 83.3% ee.

EXAMPLE 9

Optical resolution of t-butyl 2-ethyl-3-hydroxybutanoate [$R^1$=—$CH_3$, $R^2$=—$CH_2CH_3$, and $R^5$=—$C(CH_3)_3$ in formula (8)]

(1) A mixture of 15.0 g of t-butyl 2-ethyl-3-hydroxybutanoate as racemate, 9.0 g of vinyl laurate and 8.0 g of Lipase P (trade name, supplied by Amano Pharmaceutical Co., Ltd.) was stirred at 35° C. for two days. After stopping the reaction, the enzyme was removed by filtration and the enzyme was washed with n-heptane on a filter paper. n-Heptane was distilled away from the filtrate and the residue was subjected to vacuum distillation to obtain 9.9 g of t-butyl (3S)-2-ethyl-3-hydroxybutanoate, b.p. 73.5°–75° C. (4.5 mm Hg), $[\alpha]_D^{28}$=+1.5°(C=1.22, CHCl$_3$) of the following formula.

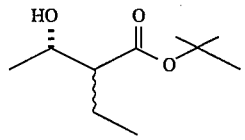

Figure 8:
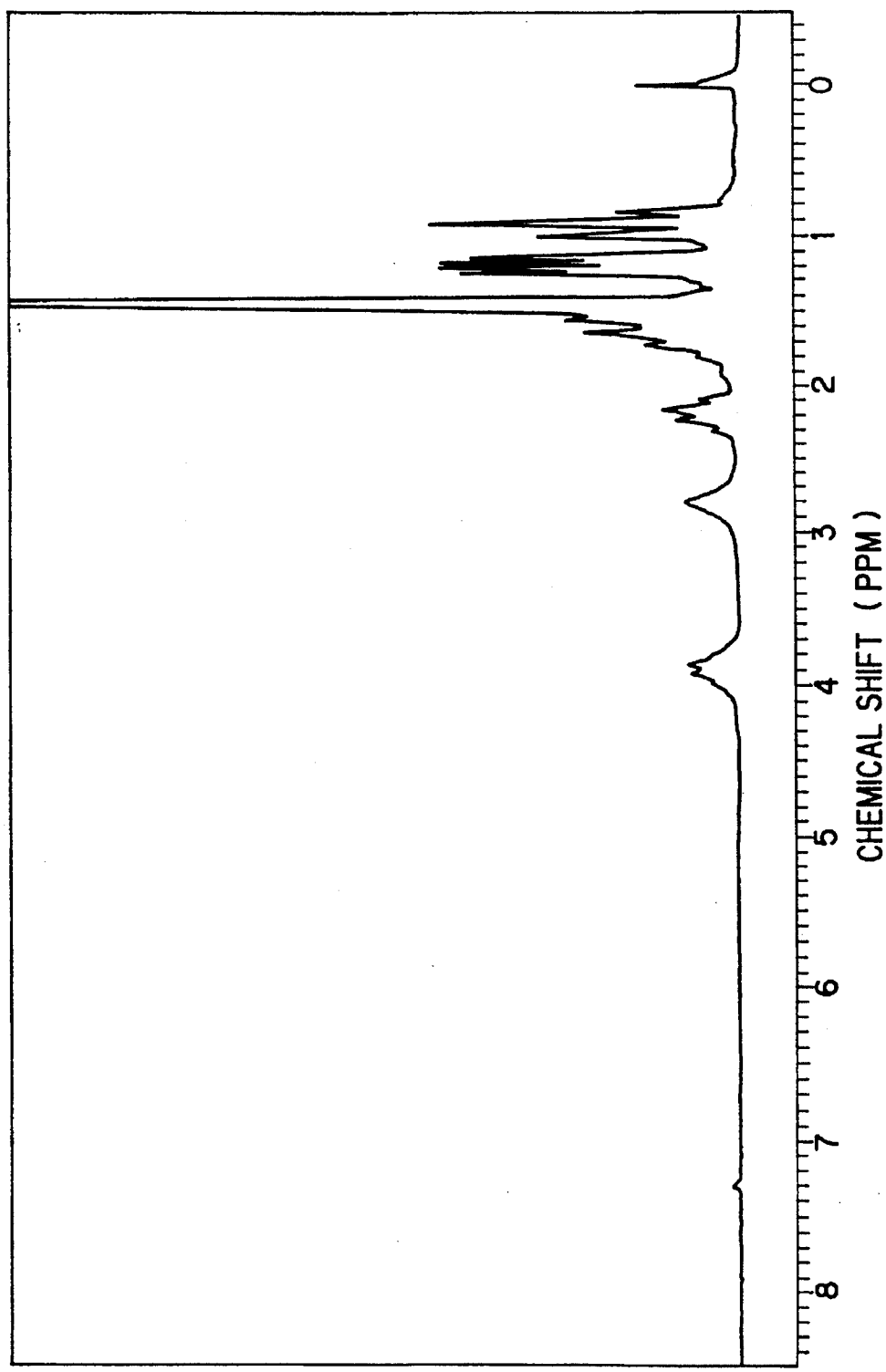
FIG. 8 shows an NMR spectrum of t-butyl (3S)-2-ethyl-3-hydroxybutanoate obtained in Example 9-(1)

The NMR chart is shown in FIG. 8.

Further, 7.7 g of t-butyl (3R)-2-ethyl-3-dodecanoyloxybutanoate was obtained.

(2) A mixture of 7.7 g of t-butyl (3R)-2-ethyl-3-dodecanoyloxybutanoate obtained in (1) above, 60 ml of methanol, and 1 ml of concentrated sulfuric acid was refluxed for 40 hours and 60 ml of water was added followed by ether extraction.

The ether phase was dried over anhydrous sodium sulfate and ether was distilled away, and the residue was distilled to obtain 1.8 g of methyl (3R)-2-ethyl-3-hydroxybutanoate of the following formula, b.p. 60.5°–65° C. (5.0 mm Hg), $[\alpha]_D^{25}$=−4.5°(C=1.30, CHCl$_3$).

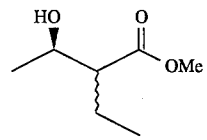

(3) According to a procedure similar to Example 1-(2), (3),(4), (2R,3R,6R)-2-trichloromethyl-5-ethyl-6-methyl-1,3-dioxan-4-one of the following formula was produced from methyl (3R)-2-ethyl-3-hydroxybutanoate.

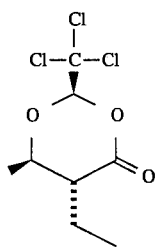

m.p. 72.4°–73.3° C.

EXAMPLE 10

Optical resolution of t-butyl 2-propyl-3-hydroxybutanoate [$R^1$=—$CH_3$, $R^2$=—$CH_2CH_2CH_3$, $R^5$=—$C(CH_3)_3$ in formula (8)]

(1) A mixture of 15.0 g of t-butyl 2-propyl-3-hydroxybutanoate as racemate, 8.4 g of vinyl laurate and 7.4 g of Lipase P (trade name, Amano Pharmaceutical Co., Ltd.) was stirred for two days at 35° C.

After stopping the reaction, the enzyme was removed by filtration and the enzyme was washed with n-heptane on a filter paper. n-Heptane was distilled away from the filtrate and the residue was subjected to vacuum distillation to give 11.1 g of t-butyl (3S)-2-propyl-3-hydroxybutanoate of the following formula, b.p. 84°–86° C. (4.1 mm Hg).

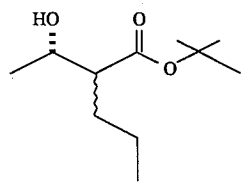

In addition, 4.5 g of t-butyl (3R)-2-propyl-3-dodecanoyloxybutanoate was obtained.

(2) A mixture of 4.5 g of t-butyl (3R)-2-propyl-3-dodecanoyloxybutanoate obtained in (1) above 45 ml of methanol and 0.5 ml of concentrated sulfuric acid was refluxed for 40 hours and 50 ml of water was added thereto followed by ether extraction. The ether phase was dried over anhydrous sodium sulfate, and ether was distilled away, and the residue was distilled and 1.2 g of methyl (3R)-2-propyl-3-hydroxybutanoate of the following formula was obtained. b.p. 76°–81° C. ( 5.0 mm Hg), $[\alpha]_D^{26}$=2.9°(C−1.37, CHCl$_3$)

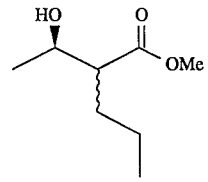

The compound was converted to (+)-MTPA ester according to a procedure similar to Example 1-(5) and the optical purity determined by $^1$H-NMR was 76% ee.

(3) According to a procedure similar to Example 1-(2), (3),(4), (2R,3R,6R)-2-trichloromethyl-5-propyl-6-methyl-1,3-dioxan-4-one of the following formula was produced from methyl (3R)-2-propyl-3-hydroxybutanoate obtained in (2) above.

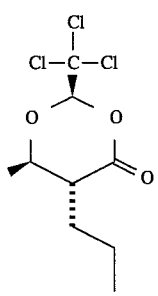

m.p. 37.7°–38.8° C., $[\alpha]_D^{26}$=–0.52 (C=0.38, CHCl$_3$)

EXAMPLE 11

Optical resolution of t-butyl 2-allyl-3-hydroxybutanoate [R$^1$=—CH$_3$, R$^2$=—CH$_2$CH=CH$_2$, R$^5$=—C(CH$_3$)$_3$ in formula (8)]

(1) A mixture of 15.0 g of t-butyl 2-allyl-3-hydroxybutanoate as racemate, 13.7 g of vinyl laurate, and 8.0 g of Lipase P (trade name, supplied by Amano Pharmaceutical Co., Ltd.) was stirred at 35° C. for 9 days. After stopping the reaction, the enzyme was removed by filtration and the enzyme was washed with n-heptane on a filter paper. The filtrate was distilled away and the residue was subjected to vacuum distillation to give 6.8 g of t-butyl (3S)-2-allyl -3-hydroxybutanoate of the following formula, b.p. 79°–85° C. (5.0 mm Hg), $[\alpha]_D^{30}$=+5.0°(C=1.35, CHCl$_3$).

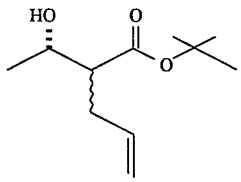

Figure 9:
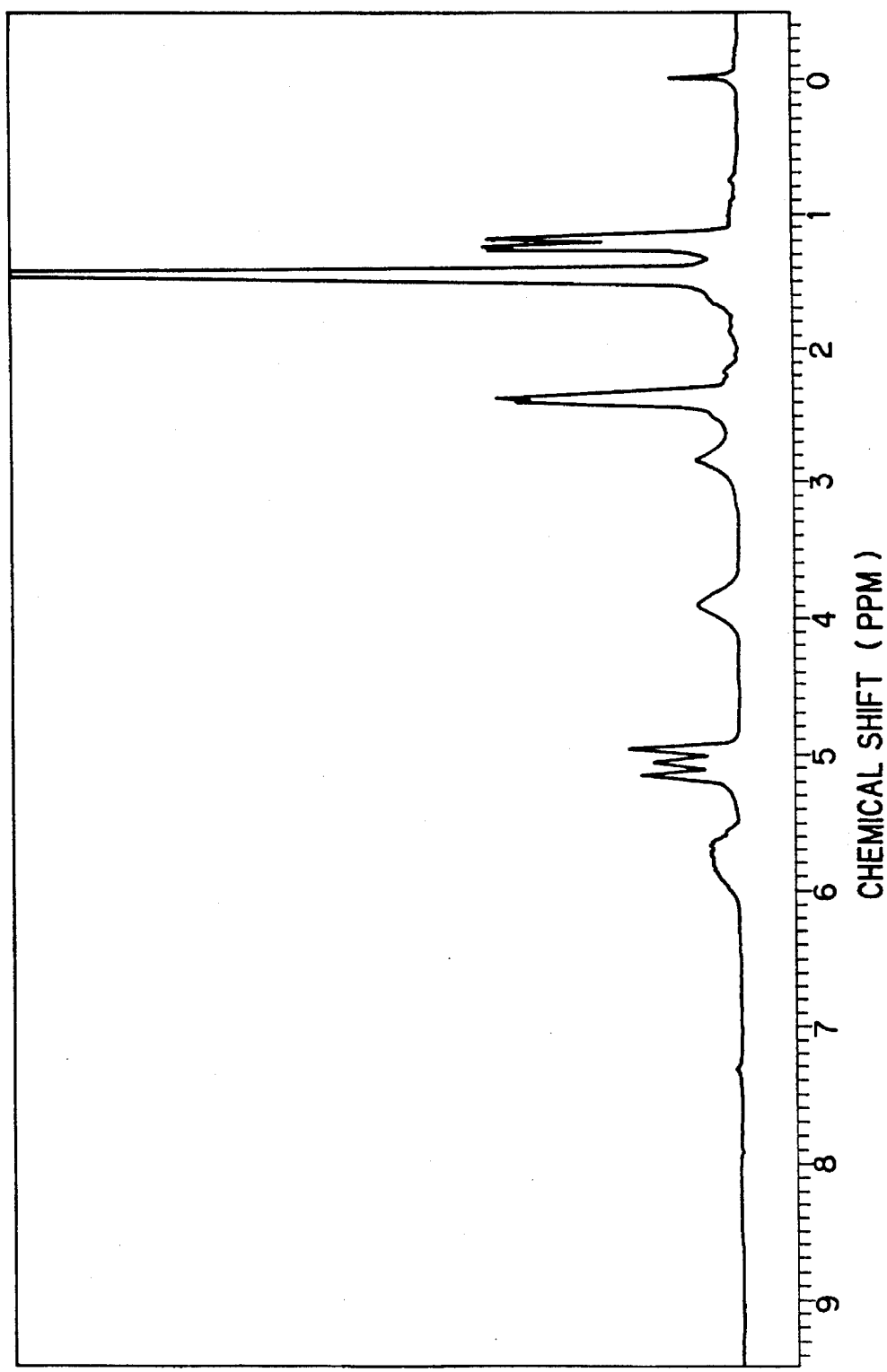
FIG. 9 shows an NMR spectrum of t-butyl (3S)-2-allyl-3-hydroxybutanoate obtained in Example 11-(1).

The NMR chart is shown in FIG. 9.

In addition, 14.1 g of t-butyl (3R)-2-allyl-3-dodecanoyloxybutanoate was obtained.

(2) A mixture of 14.1 g of t-butyl (3R)-2-allyl-3-dodecanoyloxybutanoate obtained in (1) above, 60 ml of methanol, and 2.0 ml of concentrated sulfuric acid was refluxed for 30 hours, and 60 ml of water was added thereto and ether extraction was effected.

The ether phase was dried over anhydrous sodium sulfate and ether was distilled away and the residue was distilled to give 2.9 g of methyl (3R)-2-allyl-3-hydroxybutanoate of the following formula, b.p. 59.5°–61° C. (2.0 mm Hg), $[\alpha]_D^{30}$= –5.4°(C=1.24, CHCl$_3$).

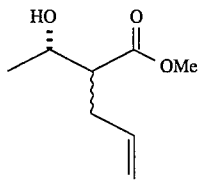

Figure 3:
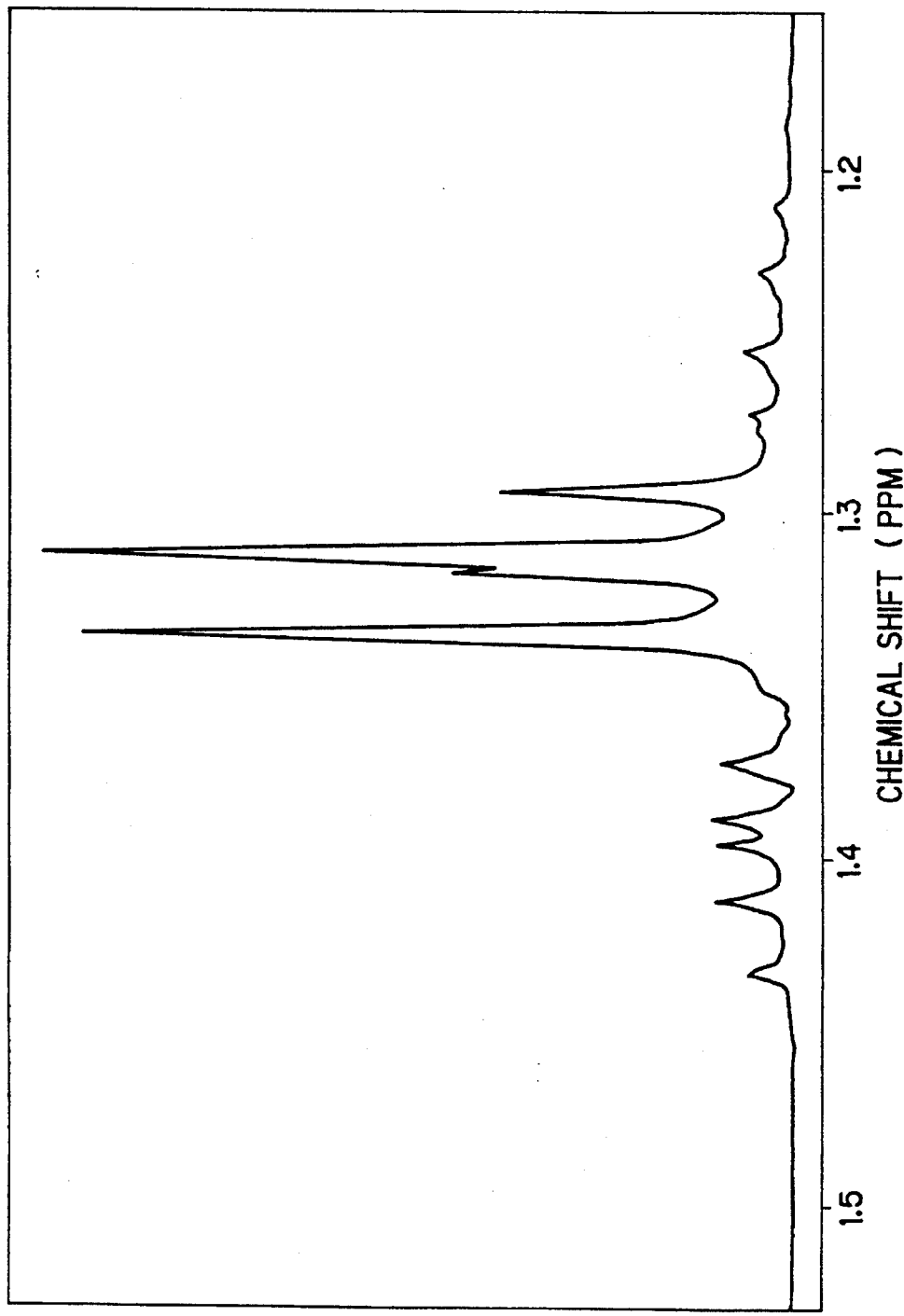
FIG. 3 shows an NMR spectrum of (+)-MTPA ester of methyl (3R)-2-allyl-3-hydroxybutanoate obtained in Example 11-(2)

This compound was converted to (+)-MTPA ester according to a procedure similar to Example 1-(5), and the optical purity determined by $^1$H-NMR was 81% ee. The NMR chart is shown in FIG. 3.

EXAMPLE 12

Optical resolution of methyl 2-methyl-3-hydroxypentanoate [R$^1$=—CH$_2$CH$_3$, R$^2$=R$^5$=—CH$_3$ in formula (8)]

(1) A mixture of 7.2 g of methyl 2-methyl-3-hydroxypentanoate, 11.1 g of vinyl laurate, and 4.0 g of Lipase P (trade name, Amano Pharmaceutical Co., Ltd.) was stirred at 35° C. for 5 days. After stopping the reaction, the enzyme was removed by filtration and washed with n-heptane on a filter paper. n-Heptane was distilled away from the filtrate and the residue was subject to vacuum distillation to give 5.6 g of methyl (3S)-2-methyl-3-hydroxypentanoate of the following formula, $[\alpha]_D^{20}$=+3.8°(C=1.26, CHCl$_3$).

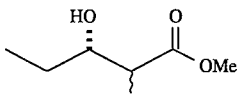

In addition, 3.6 g of methyl (3R)-2-methyl-3-dodecanoyloxypentanoate was obtained. $\alpha_D$=0.

(2) A mixture of 3.5 g of methyl (3R)-2-methyl-3-dodecanoyloxypentanoate, 12 ml of methanol and 0.5 ml of concentrated sulfuric acid was refluxed for 8 hours, and 20 ml of water was added thereto followed by ether extraction. The ether phase was dried over anhydrous sodium sulfate and ether was distilled away, and then the residue was distilled to give 0.6 g of methyl (3R)-2-methyl-3-hydroxypentanoate of the following formula, b.p. 52.5° C. (2.5 mm Hg), $[\alpha]_D^{30}$=–10.7°(C=0.61, CHCl$_3$).

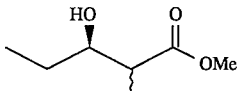

Figure 4:
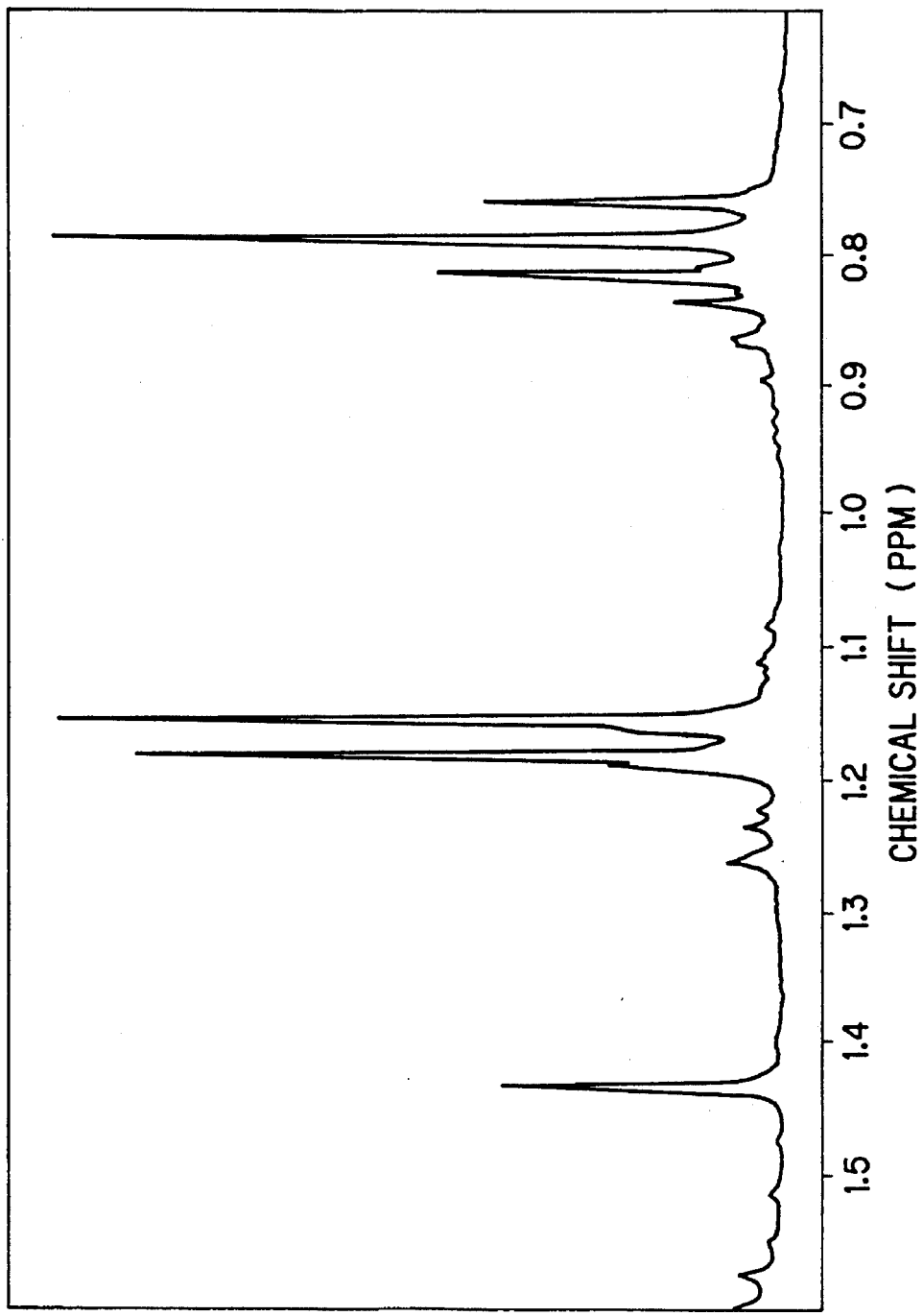
FIG. 4 shows an NMR spectrum of (+)-MTPA ester of methyl (3R)-2-methyl-3-hydroxypentanoate obtained in Example 12-(2)

This compound was converted to (+)-MTPA ester according to a procedure similar to Example 1-(5) and the optical purity determined by $^1$H-NMR was 95% ee. The NMR chart is shown in FIG. 4.

(3) According to a procedure similar to Example 1- (2), (3),(4),(2R, 3R, 6R)-2-trichloromethyl-5-methyl-6-ethyl-1, 3-dioxan-4-one of the following formula was obtained from methyl (3R)-2-methyl-3-hydroxypentanoate produced in (2).

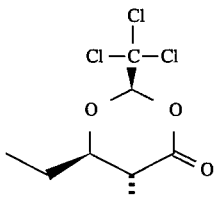

m.p. 94.1°–94.6° C.

What is claimed is:

1. A process for resolution which comprises hydrolyzing a 2-substituted-3-hydroxycarboxylic acid ester as a racemate of the general formula,

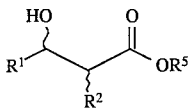
(8)

to form a 2-substituted-3-hydroxycarboxylic acid of the general formula,

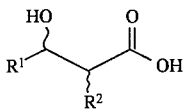
(19)

reacting the carboxylic acid with an aldehyde of the general formula,

R$^4$ C H O           (22)

to form a 2,5,6-substituted-1,3-dioxan-4-one of the general formula,

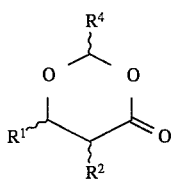 (10)

separating the resulting product into crystal and a mother liquor for recrystallization by recrystallization, effecting a ring-opening reaction of the crystal and the mother liquor residue by using an alcohol of the general formula, $R^5$ O H (23)

to resolve the racemate of formula (8) into 2,3-syn-2-substituted-3-hydroxycarboxylic acid esters of the general formulas,

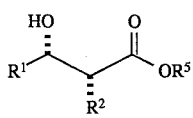 (5')

and

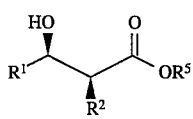 (4')

and 2,3-anti-2-substituted-3-hydroxycarboxylic acid esters of the general formulas,

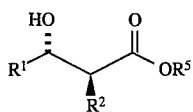 (3')

and

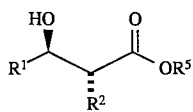 (2')

where $R^1$, $R^2$ and $R^4$ are independently selected from the group consisting of alkyl, alkenyl, and alkynyl, having 1–40 carbon atoms, the carbon chain may contain at least one member selected from the group consisting of halogen, cyano, oxygen, nitrogen, silicon, sulfur, benzene ring, cyclohexane ring, pyridine ring, pyrimidine ring, pyridazine ring, pyrazine ring, dioxane ring, bicyclooctane ring, and the rings with at least one substituent; $R^5$ is selected from the group consisting of alkyl, alkenyl and alkynyl, having 1–40 carbon atoms.

2. A process for producing an optically active compound having plural chiral centers which comprises reacting a 2,5,6-substituted-1,3-dioxan-4-one having an absolute configuration as shown in one of the formulas

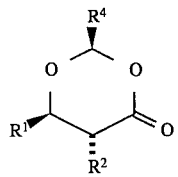 (12)

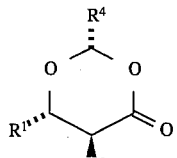 (13)

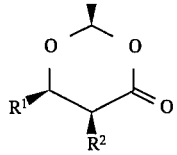 (14)

or

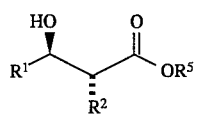 (15)

with an alcohol of the formula $R^5$ O H (23)

to produce a 2-substituted-3-hydroxycarboxylic acid ester having an absolute configuration of one of the following formulas, respectively

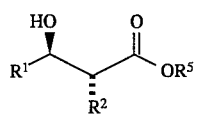 (2')

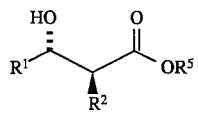 (3')

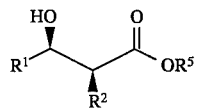 (4')

or

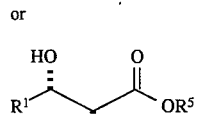 (5')

where $R^1$, $R^2$ and $R^4$ are independently selected from the group consisting of alkyl, alkenyl, and alkynyl, having 1–40 carbon atoms, the carbon chain may contain at least one member selected from the group consisting of halogen, cyano, oxygen, nitrogen, silicon, sulfur, benzene ring, cyclohexane ring, pyridine ring, pyrimidine ring, pyridazine ring, pyrazine ring, dioxane ring, bicyclo-octane ring, and the rings with at least one substituent; $R_5$ is selected from the group consisting of alkyl, alkenyl and alkynyl, having 1–40 carbon atoms.

* * * * *